(12) United States Patent
Riemer

(10) Patent No.: US 6,210,918 B1
(45) Date of Patent: Apr. 3, 2001

(54) NON-INVASIVE METHOD FOR DETECTION, DIAGNOSIS OR PREDICTION OF TERM OR PRE-TERM LABOR

(75) Inventor: Robert Kirk Riemer, Half Moon Bay, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/185,236

(22) Filed: Nov. 3, 1998

Related U.S. Application Data

(63) Continuation-in-part of application No. 08/450,126, filed on May 25, 1995, now Pat. No. 5,830,848, which is a continuation-in-part of application No. 08/198,512, filed on Feb. 18, 1994, now Pat. No. 5,508,045, which is a continuation-in-part of application No. 07/959,006, filed on Oct. 9, 1992, now abandoned.

(51) Int. Cl.[7] ........................................ C12Q 1/26
(52) U.S. Cl. .......................... 435/25; 436/510; 436/814
(58) Field of Search .......................... 435/25; 424/85.1; 530/399; 436/510, 814

(56) References Cited

U.S. PATENT DOCUMENTS

| | | | |
|---|---|---|---|
| 5,508,045 | * 4/1996 | Harrison et al. | 424/608 |
| 5,811,416 | * 9/1998 | Chwalisz et al. | 514/177 |
| 5,830,848 | * 11/1998 | Harrison et al. | 514/2 |
| 5,849,474 | * 12/1998 | Olson et al. | 435/4 |
| 5,872,126 | * 2/1999 | Cukierski et al. | 514/284 |
| 5,906,987 | * 5/1999 | Chwalisz et al. | 514/177 |
| 5,910,482 | * 6/1999 | Yallampalli et al. | 514/12 |
| 5,948,762 | * 9/1999 | Garfield et al. | 514/12 |
| 5,965,529 | * 10/1999 | Garfield et al. | 514/12 |
| 6,028,107 | * 2/2000 | Waugh | 514/563 |

OTHER PUBLICATIONS

Jaekle R. Nitric Oxide Metabolites and Preterm Pregnancy Complications. Am J Obstet Gynecol 171(4)1115–9, Oct. 1994.*

Iorio R. Nitric Oxide in Preclampsia. European J of Obstetrics & Gyn vol. 76 pp. 65–70, 1998.*

Bush P. Nitric Oxide Synthase From Cerebellum Catalyzes the Formation of Equimolar Quantities of Nitric Oxide and Citrulline from L–arginine. 185(3)960–966, Jun. 1992.*

R. Kirk Riemer, et al., Increased Expression of Nitric Oxide Synthase in the Myometrium of the Pregnant Rat Uterus, American Physiological Society, E1008–E1015 (1997).

Raj K. Bansal, et al., A Decline in Myometrical Nitric Oxide Synthase Expression is Associated with Labor and Delivery, *The American Society for Clinical Investigation. Inc.*, vol. 99, No. 10, pp. 2502–2508 (1997).

C. W. Yang, et al., Peritoneal Nitric Oxide is a Marker of Peritonitis in Patients on Continuous Ambulatory Peritoneal Dialysis, *Nephrol Dial Transplant*, 11:2466–2471 (1996).

Han Moshage, et al., Nitric and Nitrate Determinations in Plasma: A Critical Evaluation, *Clin. Chem.*, 41/6, 892–896 (1995).

Phuong Nhi Bories, et al., Nitrate Determination in Biological Fluids by an Enzymatic One–Step Assay with Nitrate Reductase, *Clin. Chem.*, 41/6, 904–907 (1995).

Laura C. Green, et al., Analysis of Nitrate, Nitrite and [15N]Nitrite in Bioligcal Fluids, *Analytical Biochemistry*, 126/1, 131–138 (1982).

Kirk Riemer, Nitrate/Nitrite Colorimetric Assay Kit (LDH Method), Cayman Clinical. No Date Given.

Michael R. L. Stratford, The Role of Nitric Oxide in Cancer Improved Methods for Measurement of Nitrite and Nitrate by High–Performance ion Chromatography, *Journal of Chromatography A.*, 770:151–155 (1970).

P. M. Rhodes, et al., The L–Arginine:Nitric Oxide Pathway is the Major Source of Plasma Nitrite in Fasted Humans, *Biochemical and Biophysical Research Communications*, 209/2, 590–596, (1995).

Ichiro Koshishi, et al., Determination of Citrulline and Homocitrulline by High–Performance Liquid Chromatography with Post–Column Derivatization, *Journal of Chromatography*, 532:37–43, (1990).

Stephen M. Sladek, et al., Nitric Oxide and Pregnancy, *American Journal of Physiology*, 272/2, R441–R463, No Date Given.

Mary B. Gilliam, et al., A Spectrophotometric Assay for Nitrate Using NADPH Oxidation by *Aspergillus* Nitrate Reductase[1], *Analytical Biochemistry*, 212:359–365 (1993.

Monica M. Epperlein, et al., Nitric Oxide in Cigarette Smoke as a Mediator of Oxidative Damage, *Int. J. Exp. Path.*, 77:197–200 (1996).

Grant W. Cannon, et al., Nitric Oxide Production During Adjuvant–Induced and Collagen–Induced Arthritis, *Arthritis & Rheumatism*, 39/10, pp. 1677–1684, (1996).

Aharon Gal, et al., Nitric Oxide Production in SJL Mice Bearing the RcsX Lymphoma: A Model for in vivo Toxicological Evaluation of NO, *Proc. Natl. Acad. Sci. USA*, 93:11499–11503 (1996).

Carl P. Weiner, et al., Induction of Calcium–Dependent Nitric Oxide Synthases By Sex Hormones, *Proc. Natl. Acad. Sci. USA*, 91:5212–5216 (1994).

(List continued on next page.)

Primary Examiner—Ralph Gitomer
(74) Attorney, Agent, or Firm—Hana Verny

(57) ABSTRACT

Methods for diagnosis, detection and prediction of preterm labor by detecting levels of nitric oxide in myometrium using non-invasive non-surgical methods for detection of nitric oxide in blood, urine, saliva, in biopsy samples or in other tissue samples. A non-invasive diagnostic procedure for detecting the onset of term labor using non-invasive or non-surgical methods.

15 Claims, 6 Drawing Sheets

OTHER PUBLICATIONS

Ronald G. Tilton, et al., Prevention of Diabetic Vascular Dysfunction by Guanidines, Inhibition of Nitric Oxide Synthase Versus Advanced Glycation End–Product Formation, *Diabetes*, 42/12 221–232 (1993).

L. Viinikka, Nitric Oxide as a Challenge for the Clinical Chemistry Laboratory, Scand. *J. Clin. Lab. Invest.*, 56:577–581 (1996).

Stephen Archer, Measurement of Nitric Oxide in Biological Models, *FASEB Journal*, 7:349–360 (1993).

Andrei M. Komarov, et al., Detection of Nitric Oxide Production in Mice by Spin–Trapping Electron Paramagnetic Resonance Spectroscopy, *Biochimica et Biophysica Acta*, 1272:29–36 (1995).

Y. Henry A. Guissani, Le Monoxyde d'azote: Un Effecteur Biologique, Detection par Résonance Paramagnétique Electronique, *Mémoire Original*, 2:157–164, (1994).

Gemma Wallis, et al., In Vivo Spin Trapping of Nitric Oxide Generated in the Small Intestine, Liver, and Kidney During the Development of Endotoxemia: A Time–Course Study, *Shock*, 6/4, 274–278 (1996).

Tetsuhiko Yoshimura, et al., In Vivo EPR Detection and Imaging of Endogenous Nitric Oxide in Lipopolysaccharide–Treated Mice, *Nature Biotechnology*, 14:992–994 (1996).

Ake Wennmalm, et al., Detection of Endothelial–Derived Relaxing Factor in Human Plasma in the Basal State and Following Ischemia Using Electron Paramagnetic Resonance Spectometry, *Analytical Biochemistry*, 187:359–363 (1990).

David M. Hall et al., In Vivo Spin Trapping of Nitric Oxide by Heme: Electron Paramagnetic Resonance Detection ex Vivo, *Methods In Enzymology*, 268:188–192, No Date Given.

* cited by examiner

NON-INVASIVE METHOD FOR DETECTION, DIAGNOSIS OR PREDICTION OF TERM OR PRE-TERM LABOR

This application is a continuation-in-part of the application Ser. No. 08/450,126, filed on May 25, 1995, issued as U.S. Pat. No. 5,830,848, issued Nov. 3, 1998, which is a continuation-in-part patent application Ser. No. 08/198,512 filed on Feb. 18, 1994, issued as U.S. Pat. No. 5,508,045, on Apr. 16, 1996 which is a continuation-in-part of patent application Ser. No. 07/959,006 filed on Oct. 9, 1992, abandoned.

This invention was made with Government support under Grant No. HD26152, awarded by the National Institutes of Health. The Government has certain rights in this invention.

BACKGROUND OF THE INVENTION

1. Field of the Invention

This invention concerns methods, agents and kits for diagnosis, detection and prediction of preterm labor or initiation of term labor during pregnancy. In particular, the invention concerns detection of levels of nitric oxide in pregnant myometrium using non-invasive non-surgical or surgical methods for detection of nitric oxide in blood, plasma, serum, urine, saliva, bioptic or other tissue samples. Additionally, this invention concerns a non-invasive and nonsurgical diagnostic procedures and kits for detecting preterm labor or initiation of labor.

2. Background and Related Disclosures

Spontaneous preterm labor and/or detection of beginning of term labor at home during pregnancy remains an increasing problem confronting the medical community.

Preterm labor, whether occurring spontaneously or the one which invariably follows any significant transuterine fetal manipulation such as needle puncture, fetoscopy, or hysterotomy for fetal surgery, presents a serious problem and is a limiting factor for all types of fetal intervention. The severe forms of spontaneous preterm labor or labor induced by an incision in the gravid uterus for open fetal surgery is resistant to all known forms of tocolysis. The management of preterm labor after fetal surgery is particularly difficult and dangerous for mother and fetus because aggressive treatment with therapeutics, such as magnesium sulfate, betamimetics and other hemodynamically-active tocolytic agents has resulted in sequelae for both mother and fetus.

Once preterm labor is diagnosed, the risks and benefits of labor inhibition must be weighed against those of allowing delivery to occur. For these reasons, the early diagnosis of preterm labor is very important.

Patients undergoing hysterotomy and fetal surgery typically experience difficulty with preterm labor despite treatments involving a regimen of preoperative indomethacin, intraoperative deep halogenated inhalation anesthesia, and postoperative administration of indocin, magnesium sulfate, and betamimetics. The majority of these patients has visible and palpable intraoperative uterine contractions often associated with fetal bradycardia from cord compression. These intraoperative contractions respond erratically to deepening anesthesia and to acute administration of magnesium sulfate or terbutaline. All the patients experience significant labor postoperatively. In mild form, such labor can be controlled by administration of intravenous tocolytics for few days. In severe form, it takes a week or longer to control postoperative labor with intravenous medication before oral or subcutaneous pump medication can be used. All patients undergoing hysterotomy eventually develop uncontrolled preterm labor, premature rupture of membranes, and premature delivery from 27–34 weeks gestation.

It would be therefore highly advantageous to provide non-surgical or non-invasive methods for early detection, diagnosis and prediction of preterm labor.

Similarly, the definite diagnosis of the beginning of the full term labor is problematic. Often, the mother either misinterprets the symptoms as the beginning of labor and is rushed to a doctor or hospital too early or misinterprets the symptoms other way around and neglects to go to the hospital on time often resulting in delivery outside of the hospital, in ambulances, etc., where the hygienic and medical care conditions for the infant and mother are less than optimal.

Thus, it would be also to the advantage of the pregnant woman to have available an easy home test for detection of imminent labor beginning.

Nitric oxide (NO) is a free radical with a very short half-life. Nitric oxide is synthesized from the amino acid L-arginine by the nitric oxide synthase (NOS). So far, the only clearly established role for nitric oxide is as a cytotoxic molecule for invading microorganisms and tumor cells. However, other physiological activity, such as acting as a neurotransmitter in the brain and in the periphery, affecting gastrointestinal tract motility and penile erection were also observed. Nitric oxide is produced in vascular endothelial cells by the nitric oxide synthase and seems to mediate vascular smooth muscle relaxation by increasing levels of cGMP. Its effect on relaxation of intrapulmonary artery and vein was described in *J. Pharmacol. Exp. Ther.*, 228:33–42 (1984).

Nitric oxide, its physiology, pathophysiology and pharmacology is described in *Pharmacological Reviews*, 43:109–134 (1991). While there were some in vitro studies described in *Brit. J. Pharmacol.*, 34:604–612 (1968) concerning the effect of nitric oxide precursors on animal isolated uterus, such studies did not lead to any conclusion or advancement useful for control of labor, particularly preterm labor in human or mammal pregnancy. Two prior patents by inventors, namely, U.S. Pat. No. 5,508,045 issued on Apr. 16, 1998 and U.S. Pat. No. 5,830,848 issued on Nov. 3, 1998, address aspects of usefulness of NO on preterm labor. These patents are hereby incorporated by reference.

The current invention provides non-surgical non-invasive or surgical methods suitable for detection, diagnosis and prediction of preterm labor, which enable clinicians to control, manipulate or inhibit preterm labor or for detection of beginning of a term labor. The methods can also be used for detection of nitric oxide synthase in surgically obtained bioptic tissue samples. The methods give a clinician and/or a pregnant woman fair warning for the imminent risk of preterm labor or timely forewarning of the impeding term labor until now unavailable. Such diagnosis, detection or prediction of preterm or term labor have not been heretofore available.

Finally, the methods provide a non-invasive diagnostic tools and kits for detecting the presence or impending onset of premature labor by monitoring levels and decreased production of inducible nitric oxide synthase expression.

All patents and publications cited herein are hereby incorporated by reference in their entirety.

SUMMARY

One aspect of the current invention is a non-invasive non-surgical diagnostic procedure for detecting the presence of impending onset of premature labor.

Another aspect of the current invention is a non-invasive non-surgical diagnostic procedure for detecting the presence of impending onset of term labor.

Still another aspect of the invention is a method for detection, diagnosis and prediction of preterm or term labor onset by monitoring levels and decreased levels of nitric oxide and/or decreased production of inducible nitric oxide synthase via decreased NOS expression.

Still yet another aspect of the current invention is a kit for detection, diagnosis and prediction of onset of preterm or term labor by detecting decreased levels of nitric oxide or decreased production of nitric oxide synthase, or decreased serum expression of NOS in biological samples such as saliva, blood, plasma, serum urine or in surgically obtained bioptic tissue samples using colorimetric, fluorometric, enzymatic, immunohistochemic, chemiluminescence, electron paramagnetic resonance or other methods.

DEFINITIONS

Figure 1:
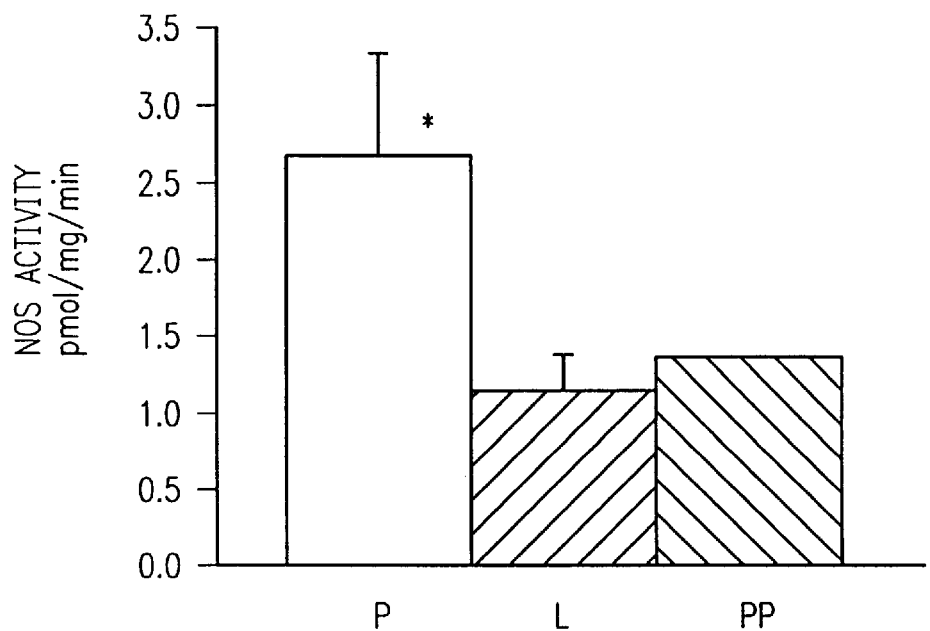
FIG. 1 depicts total nitric oxide synthase (NOS) activity in pregnant, laboring and post partum rat uterus.

As used herein, the term:

"NO" means nitric oxide.

"NOS" means nitric oxide synthase.

"eNOS" means endothelial calcium sensitive nitric oxide synthase.

"iNOS" means inducible calcium nonsensitive form of nitric oxide synthase originally identified in mouse macrophage cells.

"Agents" means compounds such as nitric oxide donor or precursor capable of potentiating the effect, or increasing the level of nitric oxide in utero and include but are not limited to S-nitroso-N-acetylpenicillamine (SNAP) and analogues thereof, nitric oxide nucleophiles or nitric oxide adducts such as diethylamino/nitric oxide (DEA/NO), DETA/NO or spermine or other nucleophilic groups known in the art, nitroglycerin and analogues thereof such as isosorbide dinitrate, nitropaste, nitropatches, nitroprusside and analogues thereof, other nitrovasodilators such as hydroxylamine, sodium azide, 2-isosorbide mononitrate, pentaerythritol tetranitrate (PETN), and analogues thereof, endogenous precursors of nitric oxide such as L-arginine or metabolic precursors of L-arginine.

DETAILED DESCRIPTION OF THE INVENTION

This invention generally concerns methods, agents and kits for detection, diagnosis, or prediction of labor during pregnancy. The methods are particularly useful for detection of spontaneous preterm or impending term labor which could, if untreated, result in premature delivery or abortion or in delivery outside of the hospital or without proper medical care.

This invention is based on a prior discovery that nitric oxide is a powerful mediator of uterine smooth muscle relaxation. Levels of nitric oxide and/or inducible nitric oxide synthase (iNOS) activity is increased during pregnancy and decline before onset of and during term or preterm labor. Exogenously supplied nitric oxide was found to stop or ablate even well established preterm labor.

The current invention provides a way of detecting the levels of nitric oxide in utero by means of detecting lower levels of NO or NOS using preferably non-invasive non-surgical methods for determining levels of nitric oxide or its enzyme nitric oxide synthase in biological samples such as urine, blood, plasma, serum, saliva or surgically obtained biopsies.

The methods of invention are preferably non-invasive and non-surgical diagnostic tools for detecting the presence or impending onset of preterm labor or normal term labor by monitoring the level of iNOS expression or level of nitric oxide in myometrium and comparing those levels to the NO or iNOS levels present in myometrium during pregnancy. For noninvasive methods, such detection of NO and iNOS levels in myometrium is by extrapolation from $NO_2/NO_3$, citrulline or arginine in urine, blood, serum, etc.

I. Nitric Oxide Levels and Detection

The presence of NO in the biological samples may be detected by conversion from the precursor, source or donor to nitric oxide, by the conversion of nitric oxide to its metabolite nitrate/nitrite or by detection and quantitation of iNOS activity.

The methods for detection of nitric oxide involve either the detection of nitric oxide synthase activity or levels of arginine (precursor), citrulline (coproduct), nitrite or nitrate (metabolites).

Nitric oxide synthase (iNOS) is the enzyme which converts nitric oxide substrate (L-arginine) to nitric oxide and citrulline. Consequently, such conversion of arginine to citrulline and the quantitation of such reaction is one of the methods used for detection of level of nitric oxide. Other methods involve enzymatic assays, measurement of levels of nitrate, nitrite, citrulline, NO, electron paramagnetic resonance, or immunological assays, immunohistochemistry, fluorescence for nitrate, etc.

The presence of iNOS in a tissue may be demonstrated histochemically with NADPH diaphorase reaction by its ability to reduce the nitro-blue-tetrazolium (NBT) dye to a blue-black formozan. The reaction is NADPH-dependent. The diaphorase reduction may be demonstrated biochemically and immunohistochemically using antibody to NOS which was previously shown to co-localize with the formazan from NOS in the central and peripheral nervous system. Because NBT changes color, this reaction may be quantitated by colorimetry detecting change in absorbance.

To develop detection methods for both NO and NOS, the following studies in vitro and in vivo were performed. The results of these studies are consistent with prior observation that the levels of NO and activity of NOS are higher in the pregnant quiescent than in the laboring uterus.

II. Diagnostic Monitoring of iNOS Levels

The invention is based on findings that certain hormones of which production in uterus is increased during pregnancy are capable of increasing the expression of the gene which controls production and activity of iNOS isoform of NOS. The capacity of the uterus to produce NO endogenously is dependent on a uterine-selective effect of iNOS in the myometrium, which in turn controls the production of NO. When the level of NO is steady, the normal pregnancy is maintained. Before and during labor or preterm labor, the level of NO substantially decreases. This phenomena is utilized for diagnosis, detection, or prediction of the onset of labor or preterm labor.

The invention, therefore, concerns methods for diagnostic monitoring of levels of NO in the myometrium either directly or preferably by extrapolation of NO levels determined in bodily fluids such as blood, serum, plasma and urine. This method provides a non-invasive diagnostic mechanism for detecting the presence, the extent, or risk of impending onset of premature labor or onset of normal labor.

The diagnostic monitoring includes but is not limited to monitoring levels of key molecules involved in NO metabolism present in blood, plasma, serum saliva, urine or other body fluids, or monitoring levels of NO and its chemical precursors, coproducts, enzymes such as arginine, citrulline, ornithine, nitrate, nitrite and iNOS.

III. In Vivo and In Vitro Studies in Animals or Humans

The role of nitric oxide in control of labor and contractions was studied in vitro and in vivo in clinically relevant monkey, sheep, rodent and human models.

The methods for labor control were studied in in vitro pregnant rat uterine tissue, in mouse uterine monocytes and in vivo in rhesus monkey model specially developed for this purpose, in sheep model, and also in controlled human clinical settings. The detailed method and results are described in the U.S. Pat. Nos. 5,508,045 and 5,830,848, incorporated by reference.

Results of these studies provide evidence that the administration, preferably by intravenous infusion of nitric oxide, of compound which is either a donor, source or a precursor of nitric oxide or inducer of endogenous tocolysis effectively suppresses the virulent uterine contractions occurring either spontaneously as preterm labor or contractions which were induced by surgical manipulation of the uterus. Infusion of nitric oxide or the nitric oxide donor or substrate suppressed and even ablated preterm labor or induced contractions.

Administration of these agents induced changes in uterine contractility through levels of nitric oxide. Infusions of normal saline or other control agents had no effect either on contractility or on maternal hemodynamics. These studies clearly show the function of nitric oxide during pregnancy and during onset of preterm or term labor.

Both in vivo and in vitro findings described below provide the background support for the current invention which concerns a method for monitoring of pregnancy and/or detection of imminent term labor or diagnosis of preterm labor by detecting levels of nitric oxide or nitric oxide synthase.

A. In Vitro Studies

Current invention is supported by in vitro studies performed on rat pregnant uterus or mice myocytes. In these studies, NOS activity was demonstrated to be present in nerves, blood vessels and decidua of gravid rat uterus by the NADPH-diaphorase staining method and by other methods. NOS activity was quantitated in subcellular fractions of pregnant, laboring and post partum rat uterus.

Results of in vitro studies confirm that NO is involved in the maintaining of pregnancy. First, NOS was found to be present in two cellular compartments. This shows that there are more than one form of NOS in the uterus and that the uterine NOS is different from other known types of NOS. Second, NOS activity is significantly decreased just before parturition and this decrease coincides with term or preterm contractions. Reduction in NOS activity at parturition shows that nitric oxide contributes to the maintenance of uterine contractile quiescence during gestation. Uterine tissue fixed during labor demonstrated markedly less NOS. Third, quantitation NOS activity in subcellular fractions of pregnant and laboring uterus revealed its presence in both the cytosylic and the membranous compartments of uterine homogenates. In both cellular subfractions, the enzyme activity decreased significantly from pregnancy to term.

For in vitro studies, isolated uterine tissue obtained from time-mated pregnant rats used according to procedure described in Example 1. Additionally, some studies were performed on mouse uterine myocytes.

1. Characterization of NOS Enzyme in Rat Uterus

In order to determine the NOS function in pregnancy and preterm labor, NOS specificity with respect to its localization was studied by determining the co-factor requirements of the NOS enzyme in crude uterine subfractions.

The crude uterine subfractions were prepared by differential centrifugation. The NOS activity was determined using the $^3$H-arginine to $^3$H-citrulline conversion assay according to *Biochem. Biophys. Res. Comm.*, 185:960 (1992).

Two distinct types of NOS activity were found in the full-thickness of uterine tissue samples. A first activity was found to be present in a particulate, membrane bound fraction pellet. This activity was not stimulated by calcium/calmodulin (SA 1.89 pmol/mg). The second activity was found in the soluble fraction (supernatant) (SA 1.64 pmol/mg protein/min). The supernatant activity significantly increases in the presence of calcium and calmodulin (CaCM).

These results show that at least two different forms of the enzyme are present in uterus: a putative membranous form which is $Ca^{++}$-insensitive and a potentially cytosylic form which can be stimulated by $Ca^{++}$. These two enzymes are different from the previously characterized NOS gene products which are known to be cytosylic $Ca^{++}$-sensitive (ncNOS), cytosylic $Ca^{++}$-nonsensitive (macNOS), or a $CA^{++}$-sensitive membranous form (ecNOS).

The particulate activity of the inducible NOS found in uterus is $CA^{++}$-insensitive and was shown to be different from the above three forms giving therefore a means for a specific detection of NOS in the uterus.

2. Comparison of iNOS Activity in Pregnant, of Actively Laboring and in Post Partum Rat Uterus In order to confirm the function of iNOS during pregnancy and its involvement in active labor, iNOS activity in subcellular fractions of actively laboring rat uterus was compared to a post partum rat uterus.

An increase in iNOS activity was found during pregnancy (P) when compared with the iNOS activity during active labor (L) and with post partum (PP) activity (FIG. 1). This difference was significant in all subfractions of the enzyme (p=0.021–0.028). INOS enzyme activity was present in both crude soluble and membranous subfractions of uterine homogenates. The production of [$^3$H]-citrulline was linear with time for up to 60 minutes. $^3$H citrulline production was dependent upon NADPH, an essential cofactor for iNOS.

Total iNOS enzyme seen in FIG. 1 was highest at 2.7 pmoles/mg/min ±0.68 in the preterm (P) 16 day pregnant uterus and declined significantly to 1.18 pmols/mg/min ±0.22 in term laboring tissue (L) or in post partum tissue (PP) to 1.4 pmols/mg/min ±0.13. In both subfractions, iNOS activity could be increased by addition of calcium and calmodulin.

Figure 2:
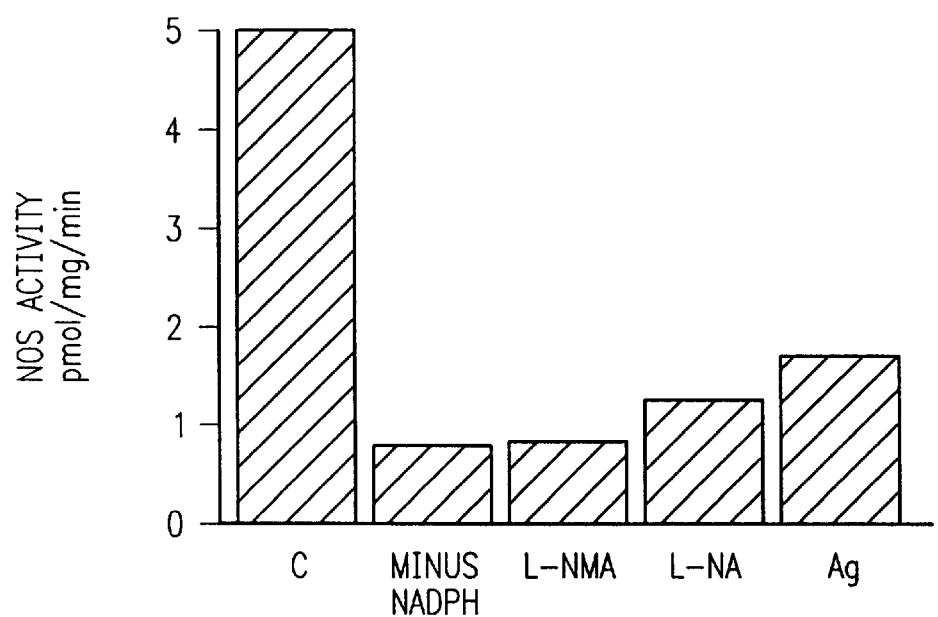
FIG. 2 depicts response of NOS activity to various NOS inhibitors.

When the iNOS activity was inhibited with L-arginine analogs, enzyme activity seen in FIG. 2 in the presence of L-nitro-methylarginine (L-NMA, 0.5 mM) was less than 20% of the total uninhibited NOS activity and in the presence of L-nitroarginine (L-NA, 0.5 mM), the NOS activity was 26% of total NOS activity. Aminoguanidine (AG, 1 mM) inhibited 34% of total NOS activity.

Ultracentrifugation of the post-mitochondrial supernatant fraction to resolve cytoplasmic and microsomal uterine subfractions verified that NOS activities measured in the more crude subfractions consisted of both cytoplasmic as well as microsomal membranous isoforms of iNOS.

These data show that the increase in iNOS activity leading to the endogenous production of nitric oxide during pregnancy occurs in a manner consistent with a role in maintaining uterine quiescence and for the retardation of labor.

The production of $^3$H-citrulline was shown to be dependent on NADPH, and was shown to be linear with time and protein concentration. Basal iNOS activity (1 mM EGTA, no added calcium) was present in both, the soluble and the particulate cellular subfractions.

Activity of iNOS and its dependency or calcium and calmodulin was different in the cytosylic and membrane fractions as well as in the pregnant and laboring uterine samples with difference in scale reaching ratio about 1:3 for cytosylic v. membrane fraction. Results are shown in FIGS. 3A and 3B.

Figure 3A:
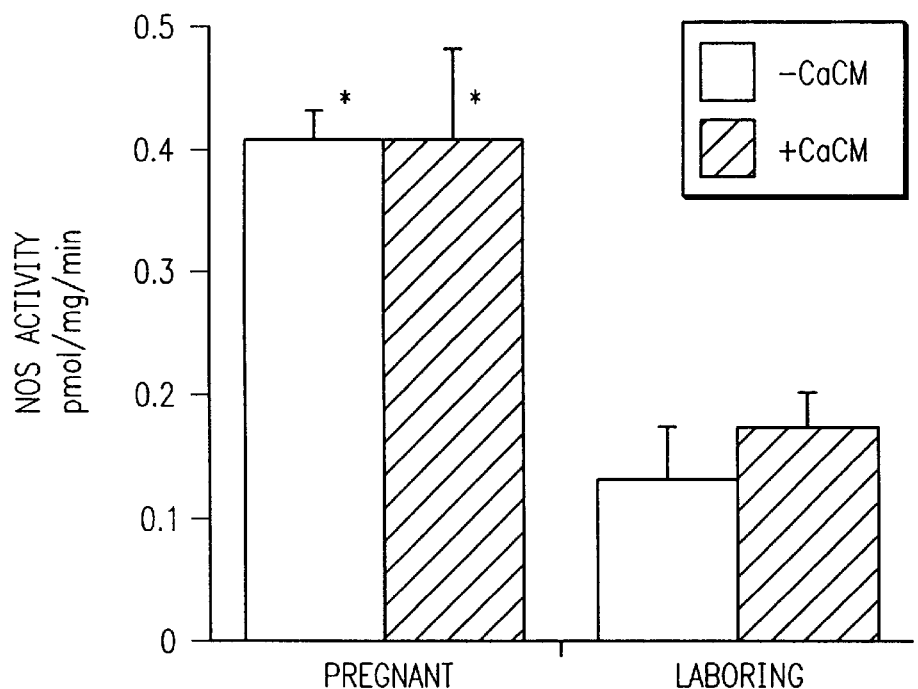
FIG. 3 depicts NOS activity found in cytosol in pregnant or laboring rat uterus FIG. 3A, and in membrane bound NOS in pregnant and laboring rat uterus FIG. 3B.

FIG. 3A illustrates activity of iNOS as determined by production of arginine to citrulline (in pmol/mg/min) found in the cytosol. iNOS activity (N=5) in the cytosylic subfraction was measured independently of calcium and calmodulin (−CaCM in white). Activity decreased significantly (p<0.05) from pregnancy to labor. iNOS activity measured in the presence of 3 mM calcium and 50 U calmodulin (+CaCM in gray) represents additional activity that is dependent on the presence of calcium. The decrease from pregnancy to labor in this group was also significant where p<0.05.

In both these groups of uterine iNOS activity found in cytosol, the activity of iNOS found in laboring uterus was significantly, about 63%, lower than in the pregnant uterus.

Figure 3B:
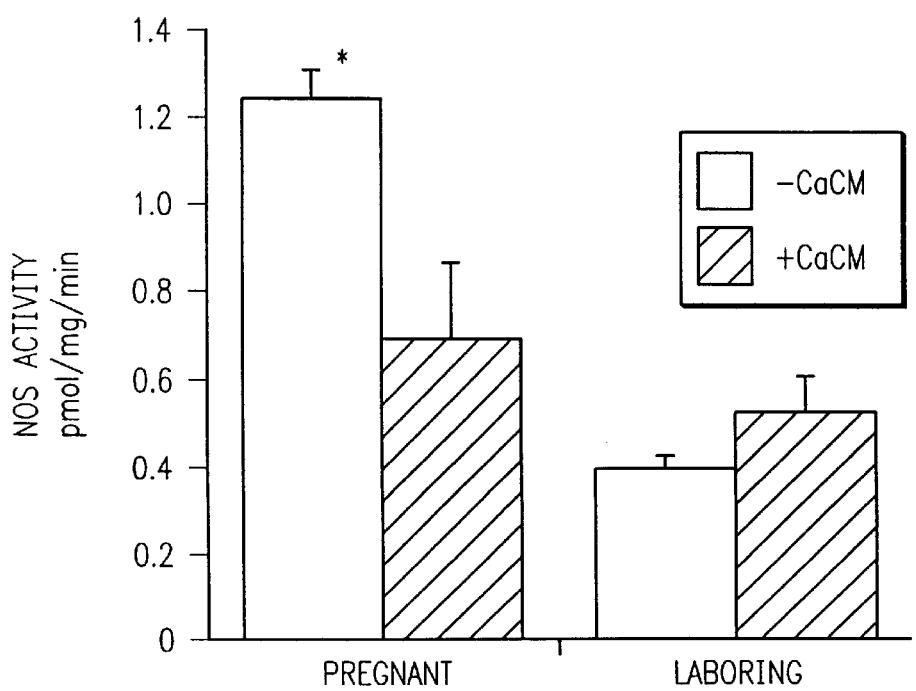

FIG. 3B illustrates iNOS activity found to be membrane bound. iNOS activity (N=5) in the particulate subfraction was measured in the absence (−CaCM) and presence (+CaCM) of 3 mM calcium and 50 U calmodulin. The decrease in iNOS activity in the −CaCM group was significant (p<0.05), while iNOS activity that was dependent upon the presence of calcium and calmodulin (+CaCM) did not change significantly from pregnant to laboring tissue. The greatest portion of the total enzyme activity was measured in the membrane bound subfraction. The total calcium insensitive iNOS activity in pregnant uterus was around 1.2 pmoles/mg/min., while the total calcium sensitive activity was around 0.7 pmoles/mg/min. As seen in Table 1 in laboring uterus, the activity of calcium insensitive NOS decreased by about 68% while the activity of calcium sensitive NOS decreased only about 25%.

The addition of calcium and calmodulin increased NOS activity. Two different enzymes, a calcium-sensitive and a calcium-insensitive form of the NOS were present in both uterine subfractions although the calcium dependent activity in the soluble fraction was minimal. In uteri of laboring rats, the basal and the calcium-stimulated activities of both the NOS enzymes were significantly reduced. Despite the fact that the overall activity of iNOS was reduced in laboring uteri, the higher activity of the calcium augmented versus the basal activity of iNOS in laboring uteri indicated a differential reduction in the calcium-insensitive isoforms(s) of the iNOS enzyme. The results obtained are shown in Table 1 below.

TABLE 1

Decrease in NOS Activity (Citrulline Production) from Pregnancy to Labor

| location | calcium dependence | % decrease in activity |
|---|---|---|
| cytosol | − | 68% * |
| cytosol | + | 59% * |
| membrane | − | 69% * |
| membrane | + | 25% |

* p < 0.05 by one way ANOVA.

Both the calcium sensitive and insensitive forms of the NOS enzyme are present in the gravid rat uterus and these activities are reduced in laboring uteri. These changes in the activities of the NOS enzymes are consistent with a nitric oxide role in the maintenance of uterine quiescence during gestation.

The presence of NOS in the different uterine structures suggests the presence of multiple molecular forms of NOS in the uterus. NOS isoforms are biochemically defined by their molecular weight, location within the cytosylic or membrane bound compartments of the cell, sensitivity to stimulation by calcium and calmodulin, and constitutive versus inducible regulation of enzyme activity.

Three major isoforms or NOS have been identified, and grouped into two major classes: constitutive calcium-dependent, and inducible calcium-independent. The activities of the two constitutively expressed forms, endothelial constitutive NOS (ecNOS) and neuronal NOS (ncNOS), are regulated by changes in intracellular calcium concentrations. The activity of the third isoform, inducible NOS (iNOS), is not controlled by changes in calcium concentration, but instead is transcriptionally regulated by a variety of growth factors and cytokines.

Figure 4A:
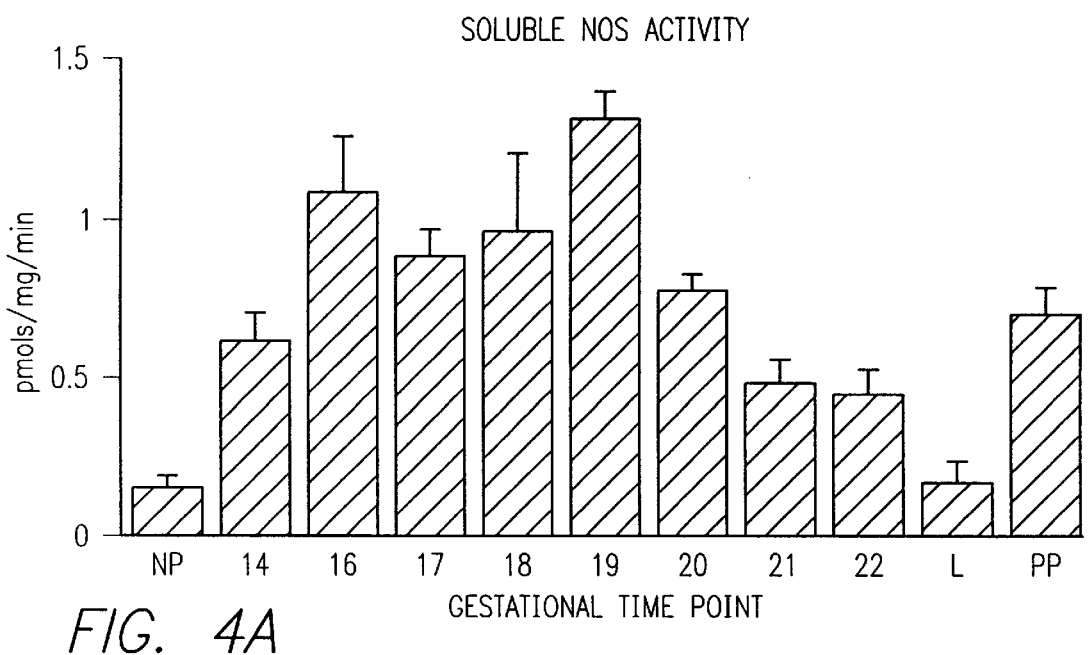
FIG. 4 is a graph depicting calcium independent NOS activity FIG. 4A in the soluble subfraction of the cell and FIG. 4B in the particulate subfraction of the cells, at varying time points before, during and after pregnancy.
Figure 4B:
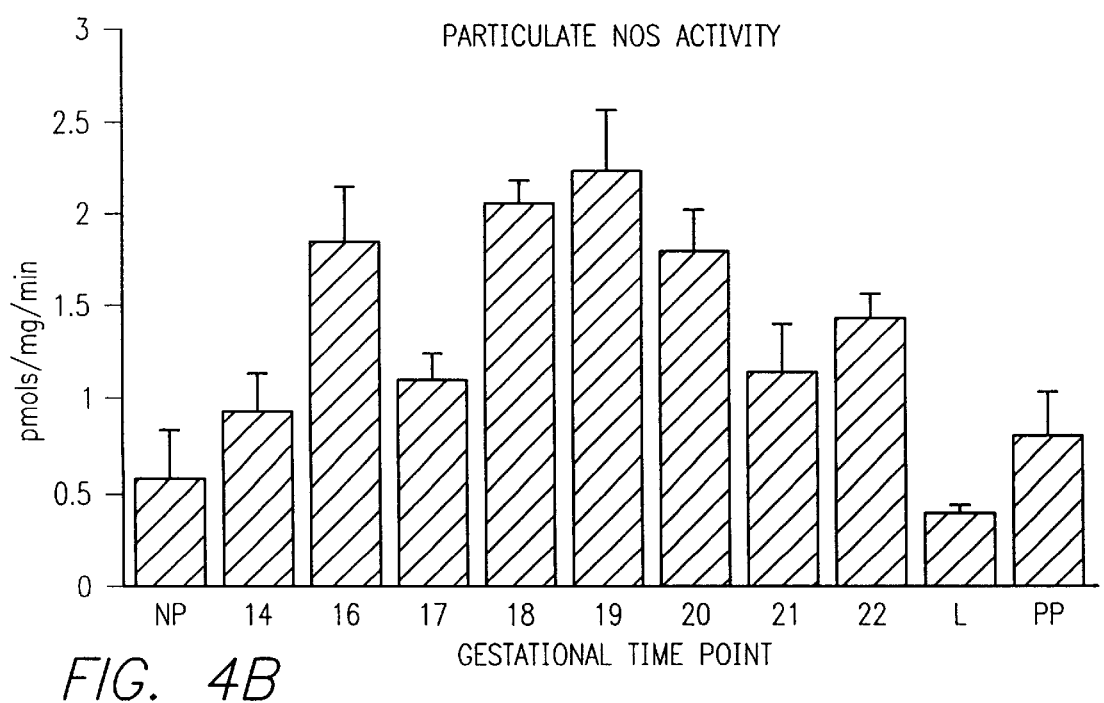

The NOS activities that underwent the greatest decline between the quiescent and laboring state of pregnancy were the calcium-independent activities present in the cytosol and membrane particulate subfractions as seen in FIG. 4 which shows activity of NOS present in the soluble and particulate fraction of the uterus during gestation.

The calcium dependent and calcium independent NOS have distinct genes each of which is able to be regulated. The major difference is their ability to increase NOS expression activity by increase in calcium ion for ecNOS and ncNOS concentrations in brain and endothelial forms. Increased expression of iNOS is not stimulated by calcium ions.

3. Decline of NOS Expression in Human Myometrium During Labor

To determine whether the decline in iNOS activity can be correlated with labor and delivery and if so what types of cells are responsible for such decline in activity the studies were performed on human myometrium in both the pregnant and nonpregnant patients.

For this purpose, cell types in human myometrium that contain inducible nitric oxide synthase (iNOS) were identified, and changes in its expression during pregnancy and labor was examined. Results show that iNOS is expressed in smooth muscle cells of pregnant myometrium. Expression of iNOS was highest in myometrium of preterm not-in-labor patients. At term, iNOS expression fell by 75%, and was barely detectable in preterm in-labor or term in-labor specimens. There was no staining in the myocytes of nonpregnant myometrium. Western blotting also revealed a similar pattern of changes in iNOS expression.

Expression of iNOS in the myocytes of human myometrium is increased greatly during pregnancy, and declines towards term or with labor. Significantly, preterm in labor patients also had a large decline in iNOS expression. These data show that changes in myometrial iNOS expression participate in the regulation of uterine activity during human pregnancy.

Figure 5:
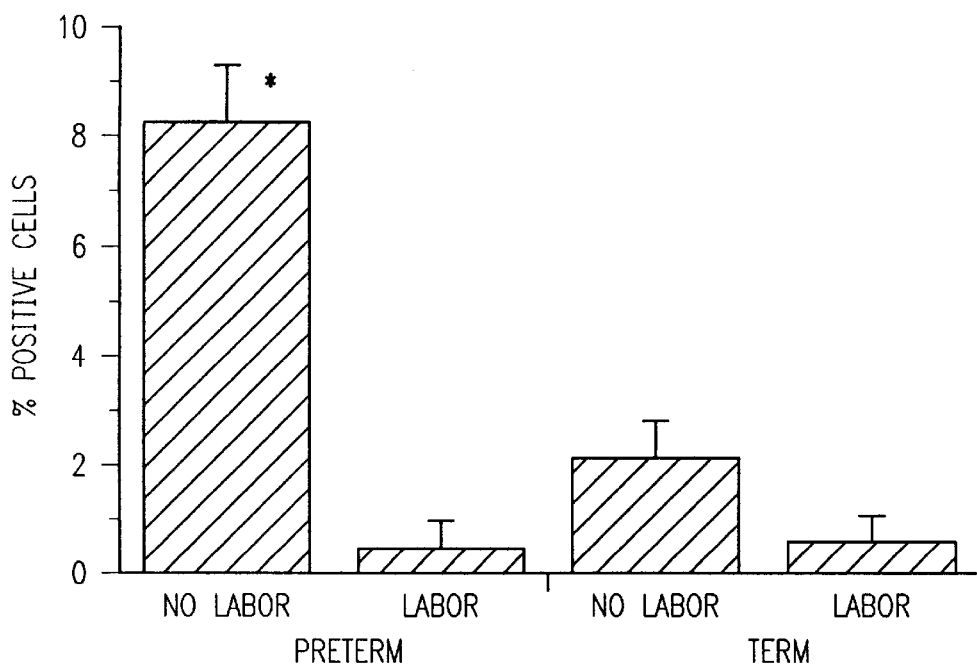
FIG. 5 shows percentage of human myocytes containing iNOS within each group of myometrial biopsies during pregnancy.

Results are illustrated in FIG. 5 which shows percentage of myocytes containing iNOS within each group of myometrial biopsies during pregnancy (mean ±SE). The numbers of patients within each group were as follows: preterm no labor, 5; preterm labor, 3; term no labor, 9; term labor, 5. *Significantly greater than each of the other three groups ($p<0.0001$). Experimental procedures are described in Example 3.

In the pregnant uteri, immuno reactive iNOS was localized exclusively in myocytes. Expression of iNOS was greatest in preterm not-in-labor samples (n=5), in which $8.2\pm1.1\%$ of the myocytes were dispersed diffusely throughout the myometrium without any obvious pattern, and did not appear histologically different from neighboring, unsustained myocytes. Staining within individual cells varied in intensity, but was mostly strong and uniform. Adjacent sections lightly counterstained with hematoxylin confirmed that the staining was in the extranuclear cytoplasm. Control sections without primary antibody, or where normal rabbit IgG was substituted for the primary antisera, showed no specific staining; this was true for all of the pregnant and nonpregnant uterine sample controls. Samples immunostained with the monoclonal antibody revealed similar staining, confirming the iNOS immunoreactivity.

Term non-in-labor samples (n=9) had significantly fewer iNOS-positive myocytes ($2.1\pm0.7\%$), and reduced staining intensity within individual cells. This group of specimens was also heterogeneous; some specimens displayed almost no staining, while some had proportions of iNOS-containing myocytes that approached the preterm not-in-labor specimens. The intensity of staining within individual cells in all of the term not-in-labor samples, however, was qualitatively less than that in the preterm not-in-labor samples. The differences within patient groups could not be correlated with any obvious clinical differences in the patients, including gestational age, medication use, or indication for cesarean section.

Samples from the two laboring groups, preterm (n=3) and term (n=5), had little or no detectable iNOS expression ($0.5\pm0.5\%$ and $0.6\pm0.4\%$), respectively. Two samples from the preterm group and one sample from the term group had no evidence of specific immunostaining. The rest of the samples in both groups showed only occasional myocytes that weakly immunostained for iNOS.

The large qualitative differences observed in iNOS immunostaining between the groups were confirmed by a quantitative analysis of the staining as seen in FIG. 5. There was a significant difference in the percentage of iNOS-containing myocytes between the four groups of pregnant myometrial samples ($p<0.0001$). Furthermore, pairwise posthoc testing (Fisher's protected least significant difference) revealed that staining in the preterm not-in-labor group was significantly greater than that in the term not-in-labor group ($p<0.0001$), the preterm in-labor group ($p<0.0001$), and the term in-labor group ($p<0.0001$). The staining in the term no-in-labor group was greater than in both laboring groups, but this was not statistically significant.

In contrast to the pregnant uterine samples, the nonpregnant uterine samples (n=4) had no detectable myocyte staining. The only immunostaining observed was in occasional cells in the connective tissue surrounding blood vessels; these cells histologically appeared to be mast cells. The staining was somewhat granular, asymmetric, and cytoplasmic in location. Histochemical staining of adjacent sections with toluidine blue revealed metachromatic purple granules in the cytoplasm of these cells, which confirms that they are mast cells. Control sections without primary antibody had no specific immunostaining.

Figure 6:
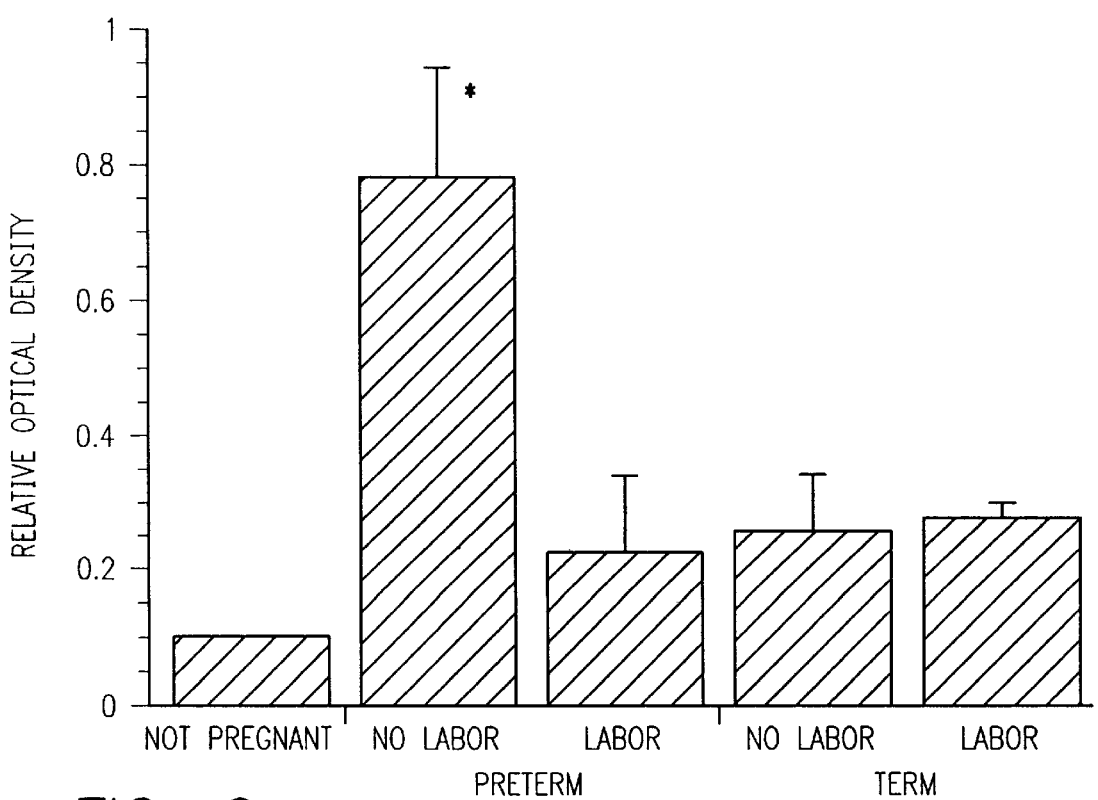
FIG. 6 shows relative optical density of iNOS in autoradiographs of Western blots for each group of myometrial protein extracts.

Western blotting of myometrial protein extracts revealed findings similar to those obtained by immunochemistry. Although equivalent amounts of protein were loaded for each sample, only pattern not-in-labor extracts contained significant amounts of iNOS. Quantitation of the relative iNOS band intensity seen in FIG. 6 revealed a significant differences between the groups ($p=0.01$). Pairwise posthoc testing confirmed that the preterm no-in-labor extracts contained significantly greater iNOS protein than the other four groups ($p<0.01$ for all).

The inducible isoform of NOS is expressed in the uterus in a pregnancy-dependent manner. Localization of iNOS mRNA reveals expression in both the decidua and myometrium. Primary uterine myocytes express NOS enzyme activity and iNOS mRNA. Increased expression of NOS in the pregnant uterus have been found to be induced in the uterus by the condition of pregnancy.

In order to determine how the signalling system for NO production is regulated, the molecular isoforms of NOS present in the uterus and the cellular sites of NOS expressions were investigated during gestation. The cDNA for NOS isolated from brain (ncNOS) from endothelial cells (ecNOS) and from macrophage (iNOS) was previously described. Putative iNOS cDNAs were isolated as a part of the invention from a pregnant mouse uterine library and are being sequenced.

iNOS gene expression

The presence of calcium-independent NOS activity in the pregnant uterus suggested that the gene for iNOS was expressed in the uterus. To confirm this, the RPA was used to measure iNOS mRNA levels in uterine samples. Messenger RNA for iNOS was present in the pregnant rat uterus at 17 days of gestation. In contrast, expression of iNOS mRNA was either not detected (nonpregnant uteri) or barely detectable (laboring uteri) by assay of RNA samples of up to 40 μg.

Immunodetection of iNOS proteins

Western blotting was used to measure the amount of iNOS protein present in the uterus and to determine whether it changed in a manner that correlated with the changes in activity and mRNA expression. All three isoforms of NOS were detected in Western blots of uterine extracts, although only ecNOS was found to be expressed at detectable levels in samples from all physiological states examined.

Figure 7:
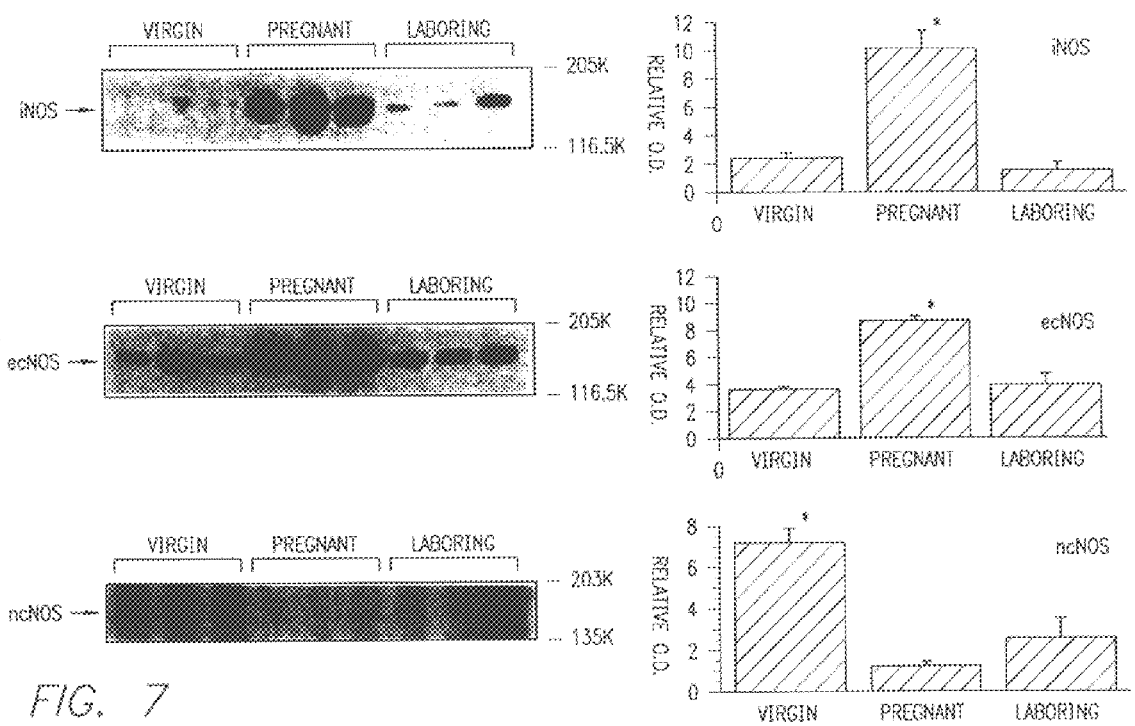
FIG. 7 shows NOS protein expression by Western blot.
Figure 8A:
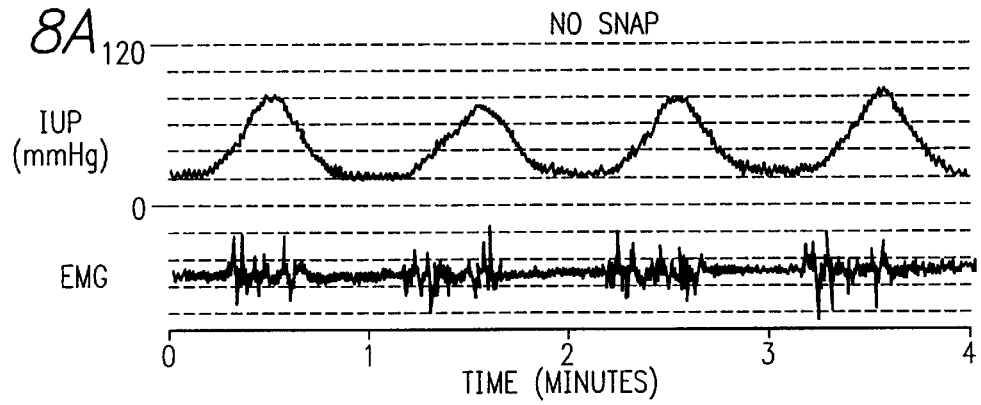
FIG. 8 is a dose response graph representing intrauterine pressure (IUP) and uterine electromyogram (EMG) of pregnant rhesus monkey experiencing preterm labor contractions in response to various doses of SNAP compared to a IUP and EMG response observed in control pregnant rhesus monkey having been given no medication.
Figure 8B:
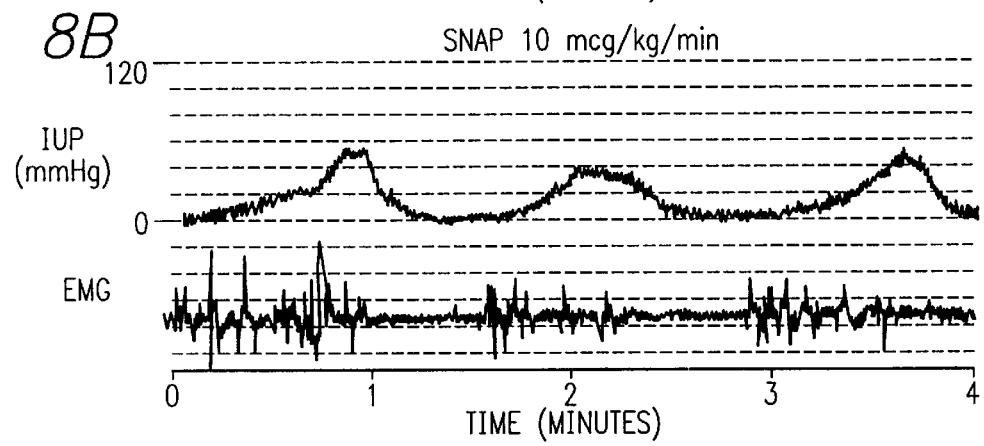
Figure 8C:
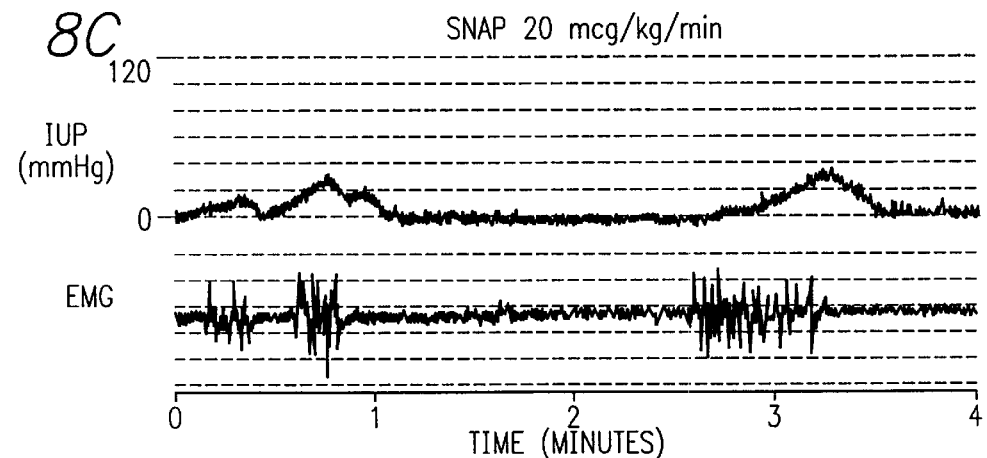
Figure 8D:
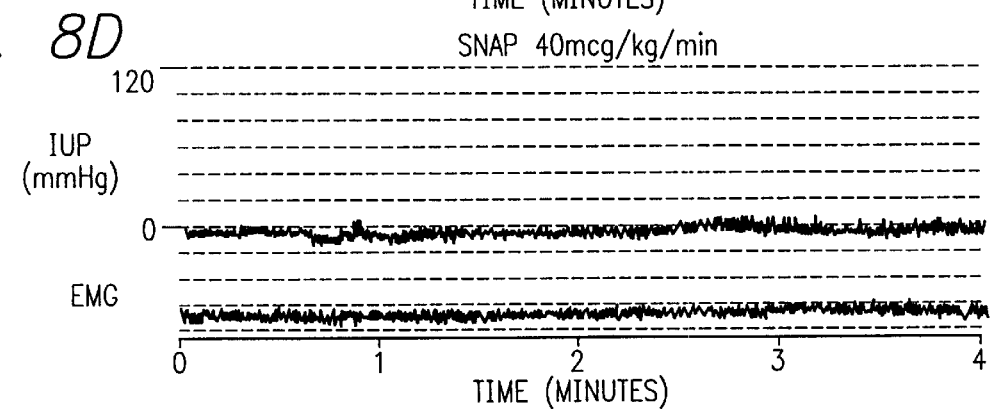

Results are seen in FIG. 7 which shows NOS protein expression by Western blot. Protein extracts (100 μg/lane) from 3 rat uteri prepared at prepregnancy and 2 points in gestation were probed with subtype specific anti-NOS polyclonal antiserums. Donkey anti-rabbit secondary antibody coupled to horseradish peroxidase was used for chemiluminescent detection. Results of densitometric and statistical analysis of autoradiograms (left) are shown in corresponding bar graphs (right). Relative molecular size of NOS bands is indicated by position of polypeptide standards whose size is laboring animals were at day 22 of gestation and had delivered at least one pup. OD, optical density, of autoradiographic signal was normalized to a reference area of same film. *P value for significance of difference for highest level of expression was compared with others using ANOVA and Scheffe's post hoc analysis: iNOS, p=0.003 (virgin), p=0.002 (laboring); endothelial constitutive form of NOS (ecNOS), p=0.08 (virgin), p=0.09 (laboring); and neutronal form of NOS (ncNOS), p=0.004 (pregnant), p=0.013 (laboring).

For iNOS, a 135-kDa band was detected in uterine extracts (FIG. 7). This band had the same mobility as the cytokine-induced protein in RAW264.7 murine macrophage cell extracts. Densitometric analysis revealed that iNOS protein expression increased nearly fivefold in pregnancy over that demonstrated in nonpregnant and laboring tissue. In contrast, ecNOS (FIG. 7) expression increased approximately twofold with pregnancy. The expression of both iNOS and ecNOS was reduced in laboring uteri at term compared with day 17–18 of gestation to levels approximating those of prepregnant uteri. The expression of ncNOS (FIG. 7) was detected in the nonpregnant but not the pregnant uterus.

Immunolocalization of iNOS Proteins

Using immunohistochemistry, we detected the expression of all three isoforms of NOS in the uterus. At day 18 of pregnancy, uterine smooth muscle cells of both the circular and longtidunial layers of the myometrium stained positively for iNOS, whereas only the epithelial cells of the decidua and glands were stained.

Vascular smooth muscle cells (and probably endothelial cells) of uterine arterioles were also found to express iNOS at this stage of pregnancy. At day 22, when labor had commenced, the intensity of iNOS staining was markedly diminished throughout the uterus. By 18 hours postpartum, iNOS staining was nearly undetectable. Staining for iNOS was not apparent in the myometrium of the nonpregnant uterus and was limited to a modest expression in glandular epithelial cells and occasional intense staining in cells in the endometrial stroma, which may be mast cells. Expression of ecNOS was detected in vascular endothelial cells of blood vessels of pregnant and nonpregnant uteri. NcNOS was detected in uterine nerve fibers coursing between the circular and longitudinal muscle layers of the virgin uteri (not shown) but was not detected in pregnant uteri.

IV. Characterization of Nitric Oxide Role in Normal Pregnancy and Preterm Labor in Mammalian Tissue Nitric oxide synthase (iNOS) is localized in myometrium, decidua, placenta, and uterine nerves. Its activity can be measured by conversion of arginine to citrulline. Changes in these areas in rat uterus were documented during pregnancy and delivery using histochemical staining as described above. NOS enzyme function was additionally assayed in non-gravid, gravid, and postpartum uterus.

Virgin, pregnant, and postpartum monkey uteri were used for nitric oxide synthase localization using diaphorase staining and arginine to citrulline enzyme assay as described in previously. In these samples, diaphorase staining was strikingly increased by pregnancy and NOS activity appeared to be concentrated in the branching neural network within the myometrium as well as in the decidua. Similarly to rat uterus, NOS activity changes were observed in monkey uterus in a progression from the non-pregnant to the pregnant and then the postpartum state. Uterine muscle strips consisting of full thickness (including decidua) or myometrium only were used to determine the layer of the uterus most responsible for nitric oxide mediated relaxation.

Studies of monkey uterus NOS activity and increase during pregnancy showed a strikingly higher diaphorase staining in gravid over non-gravid monkey uterus.

The results of in vitro studies support the current invention and confirm results of in vivo studies described below which show that nitric oxide is directly involved in maintaining uterus relaxation during pregnancy. When the endogenous levels or availability of nitric oxide decrease, the uterus respond with increased contractility resulting in labor. When this occurs prior to normal term of pregnancy, such decreased level of nitric oxide results in preterm labor. By providing exogenous nitric oxide source or donor, the preterm contractions can be inhibited and the preterm labor stopped before resulting in preterm delivery.

A. In Vivo Studies

Both the primate and sheep models and clinical studies in humans described in *Am. J. Physiol.*, 272: E1008 (1997) were used to study the in vivo mechanism by which nitric oxide mediates uterine relaxation, the role of endogenous nitric oxide production in pregnancy, the role of exogenously administered drugs that increase the level of nitric oxide, as well as their combination with other agents to determine their efficacy in the treatment of preterm labor, the timing and route of administration for clinical use, and adverse or long-term effects of these drugs on the mother, fetus or neonate.

Because of its smooth muscle relaxation activity observed in other tissues, nitric oxide was studied for its mediating activity in uterine smooth muscle relaxation on the primate model having induced preterm labor by hysterotomy.

Eleven time-mated pregnant rhesus monkeys (Macaca mulatta), having a gestational age from 106 to 137 days, and expected term of 165 days were studied.

In four monkeys of this study, nitric oxide source was administered by intravenous infusion of S-nitroso-N-acetylpenicillamine (SNAP) dissolved in 0.9% saline (0.2 mg/ml). SNAP infusion rate (range 0.625 μg/kg/min to 40 μg/kg/min) was titrated in all monkeys to maintain maternal mean arterial blood pressure (MAP) above 60 mmHg.

Results seen in FIG. 8 show that the effect of SNAP on uterine contractions was dose dependent. As SNAP infusion increased, contractions decreased in amplitude and frequency and were ultimately obliterated as seen in FIGS. 8A–D. FIG. 8A shows the dose dependency of monkey uterus contractility in a monkey experiencing severe contractions having subsequently administered 10 (FIG. 8B), 20 (FIG. 8C), and 40 (FIG. 8D) μg/kg/min of SNAP by infusion. Control monkey received no SNAP but was injected with the same volume of saline. As seen in FIGS. 8A–D, the uterine contractility index, which considers both amplitude and frequency of contractions, decreased with increasing doses of SNAP and ultimately prevented preterm labor and delivery which occurred in untreated control.

As seen from FIG. 8, SNAP in 40 μg/kg/min dose was sufficient to almost completely abate the preterm labor while the SNAP dose of 20 μg/kg/min decreased the number and strength of contractions by about 75%. The lower dose 10 μg/kg/min decreased contractions by about 30%, slowing the frequency and decreasing the strength of contractions.

Effect of substrate for nitric oxide synthase, on preterm labor inhibition was also studied. Neither the administration of the substrate, L-arginine, to the contracting uterus, nor infusion of nitric oxide synthase inhibitors into the quiescent uterus were able to change the uterine contractility index. This suggested that nitric oxide availability in the intact pregnant monkey was not substrate dependent and sensitive. However, these compounds were observed to have an effect in human patients and in other species.

The above described studies clearly show that level of nitric oxide during pregnancy plays important role. When the level of nitric oxide is maintained endogenously or exogenously, such as by providing nitric oxide precursor or source, the pregnancy can be maintained and the preterm labor averted. At the onset of the preterm labor or at the onset of normal term labor, the endogenous level of nitric oxide decreases, typically through the lower expression of inducible nitric oxide synthase resulting in decrease of the uterine nitric oxide. These findings correlate with results obtained in pregnant monkey studies receiving the NO source SNAP, described above. When the sufficiently NO contractions were observed, because SNAP was converted to NO in sufficient amount to maintain quiescent uterus. These findings unequivocally show that the endogenous level of NO controls uterine contractions. When the NO level is high, there are no contractions and no preterm labor. When the NO level decreases then there is a risk of preterm labor or the initiation of the normal term labor.

Detection of such decrease of level of nitric oxide in body fluids and/or detection of inhibition or reduction of nitric oxide production via decreased nitric oxide synthase (iNOS) expression are thus suitable diagnostic tools for monitoring pregnancy as well as for early detection, diagnosis and prediction of impending preterm or term labor.

In vivo studies were further performed in sheep model. Pregnant sheep were intravenously injected with nitroglycerin in doses from 1–3 μg/kg/min. These doses immediately abolished preterm contractions observed before. These studies confirm that the effect of individual nitric oxide donors, substrates and NOS inhibitors is species dependent and cannot be predicted without extensive experimental determination of efficacy of each individual compound in each species, including humans.

In vivo studies performed in support of this invention determined that continuous production and availability of endogenous nitric oxide is responsible for uterine relaxation during pregnancy and that a lack, decreased level, or decrease production of nitric oxide during pregnancy induces labor or parturition which is reversible upon administration of exogenous donor of nitric oxide in sufficient amount. Both the identity of the donor and the quantity of the exogenous nitric oxide donor able to reverse the labor are species dependent.

Nitric oxide was conclusively shown to play a role in labor during pregnancy. Lack of nitric oxide levels results in preterm or initiation of term labor and leads to delivery.

The preterm or term labor is effectively detected by the methods, agents or kits of the current invention which detect in biological samples obtained from a pregnant woman or mammal a level of nitric oxide or a level of nitric oxide synthase thereby monitoring the events leading to term or preterm labor contractions. Such detection allows timely treatment to assure continuation of normal pregnancy to term or timely warning to a mother that the delivery is imminent.

V. Clinical Studies

Treatment of preterm labor with known tocolytic agents, especially the virulent labor induced by hysterotomy for fetal surgery, has proven largely ineffective. Moreover, such treatment presents definite danger for both mother and the fetus because the somehow effective vasodilating concentrations of known tocolytics are too high and cause definite toxic reactions. After demonstrating in rhesus monkeys and in sheep that nitric oxide, a potent smooth muscle relaxant, ablated labor even after hysterotomy, nitroglycerin was tested during and after hysterotomy for fetal surgery in eight patients.

In an attempt to control strong hysterotomy induced contractions, it was surprisingly found that intraoperative uterine contractions responded to intravenous nitroglycerin given as a single injection or as a continuous infusion in three patients and nitroglycerin infusion was therefore used as the primary tocolytic in other patients undergoing hysterotomy and fetal thoracotomy. In contrast to all previous tocolytic regimens attempted in this setting, nitroglycerin infusion produced profound uterine relaxation and ablated postoperative preterm labor without apparent ill effect on mother or fetus.

Typically, uterine relaxation requires a depth of anesthesia which is known to produce myocardial depression in both mother and fetus. Regimen of postoperative tocolysis using magnesium sulfate and betamimetics as well as indocin proved inadequate because doses required to suppress uterine activity proved toxic for mother and dangerous for the fetus. Specifically, maternal volume restriction thought necessary to avoid pulmonary edema when using high-dose magnesium sulfate and terbutaline produces uteroplacental hypoperfusion, and indocin can produce right-heart failure manifested in patients by tricuspid regurgitation.

The effect of nitroglycerin on the preterm uterine contractions after uterine manipulation was originally studied in patients undergoing fetal surgery.

Following the hysterotomy, patients experienced several episodes of visible and palpable uterine contractions. In three patients, these contractions were treated with single intravenous doses of 50–100 μg nitroglycerin intravenously. Within 5–10 seconds the contracted uterus completely relaxed and the labor stopped. In the next two patients, the contractions were treated with an infusion of nitroglycerin. Response to demonstrated episodes of uterine contraction to nitroglycerin infusion resulted in ablation of contractions which persisted while the infusion continued.

The method of the current invention utilizes for the first time a nitric oxide donor drug for tocolytic management of preterm labor. Based on the hypothesis that nitric oxide was shown to be an important mediator of uterine smooth muscle relaxation, the ability of nitric oxide donor drugs to ablate preterm labor in the rhesus monkey and in laboring sheep, it has been now demonstrated that nitroglycerin ablates labor after hysterotomy in fetal surgery. The discovery that otherwise commonly used class of drugs has also a powerful tocolytic effect allows management of prevalent and devastating problem of spontaneous preterm labor. The potential for treating spontaneous or surgically induced preterm labor is particularly appealing because nitroglycerin and other nitric oxide donor drugs can be used effectively by a variety of routes including infusions, transcutaneous patches and sublingual depositories making chronic outpatient treatment relatively simple.

The discovery also eliminated original concerns about toxicity of nitroglycerin in pregnant women. In the studies supporting the invention, nitroglycerin infusion provided profound uterine relaxation during and after fetal surgery and appeared well tolerated by both mother and fetus. Use of nitroglycerin for tocolysis allowed reduced levels of inhalation anesthesia intraoperatively and modified the need for volume restriction and hemodynamically destabilizing drugs postoperatively. Nitroglycerin infusion does, however, require continuous monitoring of mean arterial pressure and central venous pressure in an intensive care setting.

VI. Diagnostic Methods for Detection of Nitric Oxide

Detection of nitric oxide in biological fluids and samples is difficult because the nitric oxide is very fragile in the presence of oxygen and because it is typically present in very small amounts at nanomolar concentrations.

Consequently, currently the most preferred methods for detection of NO are indirect assays such as measurements of cGMP which determines the effect of nitric oxide on granulate cyclase, measurement of nitrite accumulation which determines NO oxidation, measurement of citrulline, a coproduct of nitric oxide synthase, measurement of L-arginine, nitric oxide precursor, or measurement of iNOS, the enzyme which converts arginine to NO and citrulline.

Diagnostic methods of the invention are therefore directed to detection of nitric oxide, to the enzyme producing nitric oxide, nitric oxide synthase, nitric oxide precursor arginine and citrulline, which is a nitric oxide coproduct of the reaction producing nitric oxide from arginine, or detection of nitrate or nitrite as markers for nitric oxide or nitric oxide synthase.

These methods detect nitric oxide in body fluids, such as blood, plasma or urine or biopsies and cells of other tissues, such as myometrium cells, macrophages, endothelial cells, etc.

Nitric oxide does react readily with oxygen yielding nitrite and nitrate. These two compounds may then be detected as markers in human plasma, serum or urine.

Recovery of nitrate and nitrite markers from plasma is near quantitative (more 87%) and reproducible. Both markers are stable when frozen for more than one year. However, since nitrite is rapidly oxidized to nitrate, concentration of both must be determined to obtain correct results. The diagnostic assay is described in Example 4.

Nitric oxide also interacts with ozone and produces light. The generated luminescence is directly proportional to the amount of nitric oxide. These observations are utilized in chemiluminescence assay for nitric oxide described in Example 6.

Plasma arginine and citrulline, preferably in combination with a measurement of levels of nitrate and nitrite are valid indicators of NO generation in humans. Methods for detection of arginine and citrulline are described in Examples 2 and 5.

Electron paramagnetic resonance method is based on the finding that NO, which is a gaseous molecule, is also paramagnetic molecule with the unpaired electron in the n orbital. The basic principle of detecting radicals by EPR spectroscopy is that at a discrete amount of energy (microwave frequency) and magnetic field strength, unpaired electrons are promoted to higher energy levels. Relaxation from this state produces a characteristic spectrum.

Particularly useful in this respect became methods utilizing chemiluminescence and paramagnetic resonance (EPR).

Representative methods modified for clinical uses according to this invention are described in Examples 3–7.

Another assay for detection of level of NO in uterus or myometrium utilizes the detection of iNOS immunohistochemically, or by detection of the expression of iNOS by Western blot, by morphological staining, by qualitative and quantitative conversion assay of labeled arginine to labeled citrulline, or by any other method disclosed in the Examples and in the specification or known in the art to be suitable for detection of iNOS.

In practice, the method for detection of NO levels in uterus of pregnant women, using any method described herein, utilizes a representative number of nonpregnant, pregnant-non-laboring, term-labor and preterm labor women to determine a standard level corresponding to each of these stages.

As step one, the average level of NO in uterus and/or myometrium samples is determined for a method of choice, selected from those identified above and described herein, in nonpregnant, pregnant non-laboring, term laboring and pre-term laboring women, similarly as described in Example 3. The obtained raw data are averaged by using statistical methods used for these purposes.

The averaged data are tabulated and compared among the groups of nonpregnant, pregnant non-laboring, term laboring and preterm laboring. The same is done with bodily fluid samples collected at the same time from the same woman for each method of choice detecting NO, $NO_2/NO_3$, arginine, citrulline, iNOS, etc.

Levels of NO obtained in uterus or myometrium are then correlated with levels of NO, $NO_2/NO_3$, arginine, citrulline, iNOS in bodily fluids or in biopsies and expressed as levels of NO, $NO_2/NO_3$, arginine, citrulline, iNOS, each alone or two or more in combination corresponding to levels of NO in uterus or myometrium. Those levels are then compared to the tabulated values for nonpregnant, pregnant non-laboring, term laboring or preterm laboring women. These values are used as comparative standards for actual diagnostic testing.

For actual diagnostic testing of the patients, the level of NO, $NO_2/NO_3$, arginine, citrulline or iNOS is determined using the selected method and results are compared to the tabulated results, as obtained.

Kits for detection of NO, $NO_2/NO_3$, arginine, citrulline or iNOS may contain, for example, dip-stick containing a solid phase immobilized reagent for immunological or chromogenic detection of, for example, arginine, citrulline or nitrate/nitrite. Similarly, a reagent paper strip may contain immobilized enzymes such as urea cycle enzymes for conversion of arginine to citrulline.

Typically, there would be a solid phase having immobilized the reaction reagent, and liquid phase where the bodily fluid is brought into contact with the reagent.

For example, the kit would include the solid phase with immobilized specific iNOS antibody which would react with iNOS when iNOS is present in the sample.

Various kits and assay systems which can be easily modified for practicing the current invention are known in the art and it will be apparent to any person skilled in the art how to use this invention for its intended purpose, namely for detection of lower or higher levels of NO during pregnancy.

The detection of impeding or initiated term or preterm labor is made by comparing the higher value of NO present in pregnant non-laboring women used as a standard with decreased value of NO in the same sample type of the diagnosed patient. When the NO level is decreasing from the nonlaboring level, the risk of term or preterm labor is increasing. Quantitative correlation of both levels is an indicator of the term or preterm labor.

VII. Use of Spin Probe/Imaging agents

The detection method according to the invention may be practiced by means of introducing a spin probe and/or imaging agents by infusion over a period of time, as considered appropriate by a practitioner. Thus, a single administration or multiple administrations, e.g., daily or at other intervals, as indicated by the practitioner, may be used.

The imaging agents in accordance with this method, may be administered orally, transdermally, subcutaneously, intravenously, intraperitoneally, intramuscularly, intranasally, rectally or intravaginally. However, the most preferred route is intravenous.

One variation of the detection method is to introduce the spin probe or some means of continually releasing the imaging agent for NOS, citrulline or arginine determination as an implant, or readily injectable preparation. In the use of a liquid delivery system, the compounds may be dissolved in a liquid carrier and the like.

The present composition may be administered to a pregnant subject alone or, be it a human or non-human mammalian subject, in conjunction with other detection means known in the art acceptable for human use.

The method of the invention may be practiced by means of a single administration, or is needed, by infusion over a period of time as considered appropriate by a practitioner. Thus, a single administration or multiple administrations, e.g., daily or at other intervals or by infusion, as indicated by regimen developed by the practitioner, may be used. Typically, when the onset of preterm labor is noticed by one of many detection means, the practitioner may administer the imaging agent of the invention as described above and maintain its presence for continuous detection.

The application of the method of the invention may be discontinued when the patient reaches a point during the pregnancy term that permits parturition and the delivery of a healthy newborn.

Utility

The method for detection of term or preterm labor of the present invention may be utilized for subjects such as human and non-human mammalian females. Preferred use is the treatment of pregnant woman experiencing preterm labor, term labor or false pain which are not labor contractions or even experiencing over term pregnancy where the NOS levels are detected and conclusion reached whether or not the labor should be induced clinically. Examples of non-human mammalian animals are primates, equines, bovines, ovines, porcines, canines, felines, and rodents. Examples of other animals that may benefit from the present invention are all types of animals held in captivity such as zoo animals and pets such as canines and felines, among others. The field of animal husbandry provides a broad application for the present detection methods.

The contractile quiescence of the uterus is essential for implantation of the fertilized ovum and for maintenance of pregnancy. Despite numerous studies attempting to understand the changes that initiate parturition at term, little had been known up to the present time on how labor is triggered at term, or how preterm labor arises. A conceptual obstacle has been the lack of agreement as to whether labor is the result of a new process initiated at term or the termination of a process maintained throughout gestation. The latter concept is favored primarily because it is more consistent with the observation that the pregnant uterus remains quite refractory to a variety of stimuli. This suggests an active inhibition of contractions, which normally subsides at term. While the endogenous process by which term labor is initiated remains obscure, a more pressing clinical issue is the etiology of preterm labor. Preterm labor represents a disruption of the uterine quiescence that characterizes normal gestation. It is widely known that as a consequence of early parturition, preterm labor usually increases the rate of morbidity and mortality in neonates.

Detection of increase of the level of nitric oxide in utero or detection of enhancer expression of iNOS in a pregnant female, results in accurate and predictable initiating of labor. This invention, therefore, provides the method for detection of agents capable of detecting the level of nitric oxide sources in utero as an effective treatment for preterm labor.

EXAMPLE 1

Determination of Nitric Oxide Synthase Activity in the Pregnant Rat Uterus

This example describes methods used for in vitro studies of activity of nitric oxide synthase in non-pregnant and pregnant rat uterine tissue.

Preparation of Uterine Tissue

Uterine tissue was obtained from non-pregnant and time-mated pregnant female rats (Sprague-Dawley). Labor was considered present when at least one pup has been delivered. Animals were euthanised by ether gas overdose. The uterus was removed, fetuses, placenta and fetal membranes were separated and discarded. Uterine tissue was rinsed several times in cold isotonic saline, minced into approximately 5 mm cubes, quick frozen in liquid nitrogen and stored at $-70°$ C. for later determination of NOS activity. For morphological studies, a 1×1 cm sample of full thickness uterus was taken prior to freezing and fixed for two hours in 4% paraformaldehyde, then stored in 30% sucrose at 4° C. until processed as described below.

NOS Morphology Stains

Paraformaldehyde fixed full thickness uterine samples were examined for the presence of NOS using a tetrazolium blue dye. This method is specific for localizing NOS.

Forty micron thick floating sections of the fixed tissue were incubated for 60 minutes at 37° C. in the presence of 0.5 mM nitro blue tetrazolium (NBT) dye and 1 mM NADPH. The formation of NBT formazan product required the presence of NADPH.

Measurement of NOS Enzyme Activity

NOS enzyme activity was quantitated using the [$^3$H]-arginine to [$^3$H]-citrulline conversion assay. Previously frozen minced rat uterus was homogenized using a Tissuemizer (Tekmar). Samples were suspended in a solution containing 50 mM HEPES, 0.1 mM EDTA, 1 mM DTT, 1 $\mu$M leupeptin, 1 $\mu$M peptastatin (pH 7.5). The solution volume was four times the tissue's wet weight in grams. All homogenization and protein separation steps were performed at 4° C. Crude soluble and membranous subfractions were prepared from homogenates by differential centrifugation at 30,000 g for 20 minutes after removal of cellular debris by sedimentation at 1000 g for 20 minutes. In all preparations, the supernatant (soluble fraction) was decanted at 30,000 g for 20 minutes. In all preparations, the supernatant (soluble fraction) was decanted from the pellet (membranous fraction). Pellets were then washed to remove residual soluble protein by resuspension in 5 ml of buffer and re-centrifugation. The final pellet was resuspended in 1 ml of buffer. In one experiment purified cytosylic and microsomal subfractions were prepared for the purpose of demonstrating the relative proportion of NOS activity in these two subfractions, and to compare this with the crude separations. Homogenates were centrifuged at 10,000 g for 20 minutes and the resulting post-mitochondrial supernatant was subjected to ultracentrifugation at 105,000 g for 60 minutes.

Samples of the cellular subfractions (50 to 100 μg protein) were incubated at 37° C. for 45 minutes in 50 m MHEPES buffer (pH 7.5) containing 1 mM NADPH, 14 μm tetrahydrobiopterin, 5 μM FAD, 1 mM EGTA, 1 mM magnesium chloride, 5 μM L-arginine and 15 nM [$^3$H]-arginine (Specific activity: 77 Ci/mmol) obtained from Amersham. Calcium-sensitive NOS activity was determined by addition of 3 mM $CaCl_2$ (resulting in a total free calcium concentration of 2 mM), and 50 units bovine brain calmodulin (Calbiochem, San Diego) to aminoguanidine (0.5 mM each) to the incubations. All reactions were stopped by dilution with ice cold stop buffer (5 mM HEPES, pH 5.0) and labeled citrulline was separated from labeled arginine by ion exchange chromatography on 1 ml columns of Dowex 50W-X8 (Na form) resin. [$^3$H]-citrulline was quantitated by scintillation coating (Safety Solve, Research Products, Inc.). Total protein concentration was determined using Coomassie reagent (Bio-Rad). Protein was dissolved in 1.5 N NaOH and bovine serum albumin was the standard. Enzyme activity is expressed in pmol [$^3$H]-citrulline/mg protein/minute.

Isolation and analysis of RNA

Whole uterine RNA was prepared from nonpregnant, 19-day pregnant, and laboring rat uteri after sterile removal from animals using TriReagent (Molecular Research Center, Cincinnati, Ohio) according to the manufacturer's protocol. RNA concentration was determined by ultraviolet light absorbency, and aliquots were stored as ethanol precipitates at −20° C. An iNOS cDNA template was generated by polymerase chain reaction (PCR) amplification of mouse liver cDNA using oligonucleotides flanking a region of the putative heme binding domain. This region has minimal homology between NOS isoforms. The oligonucleotides (oligo) had the following sequences: oligo 1: 5' TTTCAGCACATCTGCAGACACATATTT-3' (SEQ ID NO: 1) and oligo 2: 5'-ACTATGGAGCACAGCCACACATTGATCAC-3' (SEQ ID NO: 2).

The amplified product was ligated into the PCR-II vector using the TA Cloning System (Invitrogen, San Diego, Calif.), and its sequence was determined to be identical to bases 836–1441 of the murine iNOS sequence. The 606 bp PCR product, excised from PCR-II as a Bam H1-Xba fragment, was subcloned into the Bluescript II vector (Stratagene, La Jolla, Calif.) for riboprobe synthesis. After linearization of the template at an Nco-I site, a 370 bp iNOS cRNA probe was transcribed using T3 RNA polymerase (Stratagene) and [α-$^{32}$P]rUTP (NEN, Boston, Mass.). A cRNA probe for rate 18S rRNA was included with the iNOS probe to monitor sample recovery on a per-sample basis. Uterine RNA (40 μg) was used for ribonuclease (Rnase) protection analysis (RPA).

Hybridization of RNA probes to sample RNA, Rnase digestion, and isolation of the protected fragments were carried out with the use of the RPA-II assay kit (Ambion, Austin, Tex.). A 5% polyacrylamide-8 M urea denaturing gel was employed to resolve protected fragments. Within the murine iNOS probe sequence used, there are 11 mismatches to the rat iNOS sequence. Hybridization of the mouse probe to rat iNOS mRNA results in a protected fragment that is only ~30 bases shorter than the fragment protected by mouse iNOS mRNA, suggesting that most of the mismatches do not disrupt hybridization sufficiently to render the hybrids susceptible to Rnase.

NOS detection by Western blot

Uterine protein extracts were prepared by homogenizing tissue in 5 vol (1 ml/g wet wt) of boiling 10 mM tris (hydroxymethyl)aminomethane (Tris) HCl, pH 7.4, containing 1% sodium dodecyl sulfate (SDS), heating the homogenate in a microwave oven for 10 sec, followed by centrifugation at 7,500 g for 15 min (15° C.) to remove insoluble debris. Protein extracts from induced and noninduced RAW264.7 murine macrophages (14) served as controls for iNOS. Electrophoresis was performed using 100-μg aliquots of protein extracts from nonpregnant, 17 and 19-day pregnant, and laboring rat uterus in 1×loading buffer (final concentration: 1% SDS, 2.5% β-mercaptoethanol, 5% glycerol, and 0.0025% bromphenol blue in 0.025 M Tris HCl, pH 6.8) in a 6% SDS-polyacrylamide gel electrophoresis. Western blotting was performed after electrophoretic transfer of resolved proteins onto Immobilon-P membranes (Millipore, Bedford, Mass.). Mouse monoclonal antiserums (Transduction Labs, Lexington, Ky.) to iNOS (no. N39120), diluted 1:1000) and ecNOS (no. N30020, diluted 1:2500) were used. A rabbit polyclonal antiserum (see below) to ncNOS was used at a dilution of 1:1000.

An ncNOS antiserum was produced by immunization with an *Escherichia coli*-expressed cDNA fragment of ncNOS synthesized using standard procedures by reverse transcriptase PCR of maternal rat cerebellar mRNA. The first 1,270 bases of the ncNOS gene coding sequence were amplified by using the primers oligo 3: 5'-TTTGGATCCATGGAAAGAGAACAAGCC-3' (SEQ ID NO: 3) and oligo 4: 5'-GCTTGGACCACTGGATCC-3' and sequenced on both strands to confirm its correspondence with bases 349–1618 of ncNOS cloned by Bredt et al., *Nature*, 351:714 (1993). The ncNOS cDNA fragment was subcloned into the plasmid pET-23a (Novagen) for expression in the DH5-α strain of *E. coli*. The pooled isopropyl-thio-β-D-galactopyranoside-induced supernatant was diluted with an equal volume of 2×loading buffer and electrophoresed through a 12% SDS polyacrylamide gel. The gel was rinsed twice in distilled water, and the bands were visualized with KC1-DTT staining. The band corresponding to the ncNOS protein was then excised, minced through an 18-gauge needle, then lyophilized, and used for immunization without further purification. Approximately 500 μg of partially purified ncNOS fragment was mixed with Freunds adjuvant and injected intradermally into New Zealand White rabbits. The same quantities were given as boosters at 2, 4, and 6 week, and blood was then collected 14 days later. Serum was separated from the clotted blood, stored at −80° C., and used without further purification. The ncNOS antiserum and an antiserum to the iNOS fragment produced by the same techniques were found to identify bands of correct molecular sizes when tested against samples of positive control tissue extracts (rat cerebellum and cytokin-induced RAW264.7 cells, respectively).

A horseradish peroxidase-conjugated donkey anti-rabbit secondary antibody (Amersham) was used with Pierce (Rockford, Ill.) Supersignal substrate to detect the NOS bands. Quantitation of the results of Western analyses of uterine extracts from three animals at each time point was conducted by scanning densitometry (Bio-Rad) of the autoradiograms in which the optical density (OD) for equal areas of the band of interest was compared with a reference area of the film and expressed as the relative OD.

Immunolocalization of iNOS

Specimens used for the detection of iNOS were fixed in Histochoice (Amresco, Solon, Ohio) at 4° C. for a minimum of 24 hours. The detection of iNOS was found to be unreliable in paraformaldehyde-fixed tissues. Fixed specimens were paraffin embedded and sectioned at 7–9 $\mu$g. To quench endogenous peroxidase activity and permeabilize the tissue, deparaffinized sections were treated with a solution of 0.1% hydrogen peroxide containing 1 mg/ml of saponin (Sigma, St. Louis, Mo.) for 15 minutes. After washing immunostaining was performed in batch for comparison between different gestational ages, with a control section where primary antiserum omitted, processed on the same slide as the experimental. Detection of iNOS was unsatisfactory with the avidin-biotin-peroxidase method (Vecatastain Elite Kit, Vector Labs, Burlingame, Calif.). Therefore, the peroxidase-antiperoxidase (PAP) technique was used. Affinity-purified anti-iNOS polyclonal serum (no. SC650, Santa Cruz Biotechnology, Santa Cruz, Calif.) was incubated at a concentration of 2 $\mu$g/ml overnight at 4° C. in blocking solution composed of Tris-buffered saline (10 mM Tris Cl, pH 7.4, 0.9% NaCl) containing 1% fish gelatin (Sigma). After unbound primary antiserum was washed away, the sections were incubated with a 1:100 dilution of goat anti-rabbit immunoglobulin G affinity-purified heavy plus light chains (ICN, Irvine, Calif.) for 30 minutes at room temperature, washed, and then incubated with rabbit PAP (Cappel, Durham, N.C.) at a dilution of 1:100. Diaminobenzidine was used as the peroxidase substrate, and the tissue sections were counterstained with hematoxylin to distinguish the cell nuclei. Specificity of iNOS immunostaining was confirmed by producing the identical staining results with the use of the iNOS monoclonal antiserum (Transduction Labs) used in the Western analysis and an anti-iNOS polyclonal antiserum we produced from bacterial-expressed protein, which also produced an identical pattern of immunostaining.

Statistical Analysis

NOS activity data are reported as means ±SE. One analysis of ANOVA was used to evaluate differences in enzyme activity at different times in gestations, and the 95% confidence level of significance was used.

EXAMPLE 2

The Methods Used for Detection of Expression of Various NOS Isoforms

This examples illustrates the methods used for detection of expression of various NOS isoforms.

Preparation of Soluble and Membranous Particulate Subcellular Fractions

Uterine tissue was removed aseptically from the abdomen and rinsed in normal saline (4° C.) to remove blood. The vessels penetrating along the axis, the placentas and amniotic sacs were removed, and the uteri were opened along their longitudinal axis, the placentas and amniotic sacs were removed, and the uteri were rinsed again. For studies of NOS in the decidua/endometrium, the decidua was removed by scraping with a scalpel blade, repeated rinsing, and collection of the scrapings by centrifugation of the rinse solution. The tissue was then either frozen using liquid nitrogen and stored at −70° C. (enzyme assay, RNA preparation) or used without freezing. Frozen samples retained their NOS activity. Samples for Western blot were stored frozen at −70.

Western blotting analyses was performed as described in *Endocrinology*, 132:1609 (1993). Samples for morphological study, in situ hybridization, immunocytochemistry and histochemistry were pinned to dental wax at physiologic length, fixed in 4% paraformaldehyde, 0.1 M $NaPO_4$, pH 7.4 for 2 hours, stored overnight in 30% sucrose then imbedded in OCT and stored at −70° C. for later cryostat sectioning.

Uterine tissue was homogenized in 4 volumes/wet weight in 50 mM HEPES pH 7.6, supplemented with protease inhibitors using a Tissuemizer (2×5 sec at 80% power). Cellular debris and unbroken cells were sedimented at 1000×g, and the supernatant recentrifuged at 30,000×g to produce a crude soluble fraction, and a membrane particulate fraction. Since the enzyme activity was present in crude cellular subfractions it did not have to be extensively purified to assay. When appropriate, a 10,000×g post-mitochondrial supernatant were further processed by centrifugation at 100,000×g for 30 minutes to produce true cytosylic and microsomal membrane preparations to verify the cellular subfraction in which the NOS activity resides. The membranous subfraction was extensively washed and recentrifuged to remove any contaminating soluble activity. Extractability of the membranous activity was assessed in the presence of 1 M KCl to determine whether any putative membranous activity consists of soluble activity which is associated with the membrane in a change-dependent manner as has been found for bNOS expressed in human but not rat skeletal muscle.

Nitric Oxide Synthase Activity

For most assays, enzyme activity was measured by the conversion of arginine to citrulline.

Arginase activity is a potential contaminant of the soluble NOS preparations. This activity was evaluated in the mouse and rat uterine preparations, and it has been determined that it is unlikely to complicate the NOS determinations because it is not inhibited by either aminoguanidine or L-NAME, the two NOS inhibitors which were used to define NOS activity. Further verification was done to assess the extent of ornithine production in the labeled arginine studies by HPLC separation of metabolites.

Conversion of $^3$H-arginine to $^3$H-citrulline

The assay was performed by monitoring the formation of $^3$H-citrulline from $^3$H-arginine by methods described in *BBRC*, 185:960 (1992).

Enzyme reactions were carried out at 37° C. containing 50 to 300 $\mu$g of protein, 1 mM NADPH, 16 $\mu$M tetrahydrobiopterin, 5 $\mu$M FAD, 10 mM $MgCl_2$, 100 to 400 $\mu$M unlabeled L-arginine and 15 to 50 nM $^3$H-arginine (SA 69 ci/mmol), and other effectors (calmodulin and calcium) under conditions which drive the reaction at maximal velocity. For all NOS activities measured, linearity of velocity was tested with time and protein, optimal incubation time, optimal concentrations of all cofactors and effectors, and the Km and Vmax for the activities were determined.

The cofactors, $^3$H-arginine, and protein mixtures was incubated for 30 minutes and the reaction stopped by the addition of ice cold Stop Buffer: 50 mM HEPES, pH 5.0, with 1 mM L-citrulline. All NOS activity was defined by the ability to be inhibited by the competitive antagonists L-NAME, NMA, LNA or aminoguanidine, the optimal concentrations of which (ca 100 to 1000 $\mu$M) was determined in preliminary experiments. Stopped samples (2 ml) were spiked with $^{14}$C-citrulline to monitor column recovery (which is generally about 70%), and applied to columns containing 1 ml of Dowex AG50W-X8 resin, Na+ form, and $^3$H citrulline was resolved from substrate arginine and quantitated by scintillation counting.

The Bradford assay in *Anal. Biochem.*, 72:248 (1976), was employed to determine the concentration of total protein in all samples. Bovine serum albumin was used as a standard. Enzyme activity was reported in pmol/min/mg protein. Validation of the Dowex chromatographic method was HPLC separation on SCX column.

EXAMPLE 3

Detection of Decline of Myometrial Nitric Oxide Synthase Expression Associated With Labor and Delivery This example describes materials and methods used for detection of decline of myometrial nitric oxide.

Five groups of patients were studied: (a) nonpregnant, (b) preterm not-in-labor, (c) term not-in-labor; (d) preterm in-labor, and (e) term in-labor. Nonpregnant specimens were obtained from premenopausal women aged 41–48 years undergoing hysterectomy for menometrorrhagia. Myometrium was sampled from the supraisthmic region of the uterus, taking care to avoid any endometrium or serosa. All pregnant specimens were obtained at the time of caesarean section from the myometrium of the upper edge of the hysterotomy incision. The pregnant patients (aged 18–38 years) were grouped by both gestational age (term, 37–41 weeks; preterm, 26–34 weeks), and by whether or not active labor was present. All laboring patients had regular painful contractions with cervical dilation >3 cm. All nonlaboring patients had neither cervical change nor preceptible regular contractions. Term patients had cesarean sections because of cephalo-pelvic disproportion, prior uterine incisions, fetal malformations, and breech presentation. Pre term in-labor patients had cesareans for breech presentation and placenta previa. Preterm not-in-labor patients had cesareans for fetal distress, breech presentation, placenta previa, cervical cancer, and maternal pheochromocytoma. The study was approved by the Committee for Human Research of the University of California, San Francisco, and patients were given appropriate informed consent.

Immunohistochemistry

After collection, a cube of each tissue specimen, approximately 5×5×5 mm and grossly devoid of decidua or serosa, was fixed by immersion in a solution containing in final concentrations 4% formaldehyde, 0.1 M phosphate buffer (pH 7.6), and 50% methanol for at least 24 hours at 4° C. The specimens were paraffin-embedded, sectioned at 8 µm, and collected on saline-coated glass slides. Sections were then deparaffinized in xylene, rehydrated through graded alcohols, and equilibrated in 0.05 M Tris-buffered saline (TBS), pH 7.4. Endogenous peroxidase activity was quenched in 2% $H_2O_2$ in 60% methanol; the tissue was permeabilized with 0.2% Triton X-100 in TBS, and nonspecific binding was blocked with 2% normal goat serum in TBS (blocking solution).

Immunostaining was conducted with a rabbit polyclonal antibody specific for iNOS (No. N32030; Transduction Labs, Lexington, Ky.) which was provided as an IgG fraction affinity-purified against the peptide immunogen. The antiserum was diluted to 5 µg/ml in blocking solution, and was incubated on sections overnight at 4° C. After washing in TBS, sections were exposed to two sequential cycles of 1:100 goat anti-rabbit IgG, and 1:100 rabbit peroxidase-antiperoxidase complex (20 mg/ml stock concentration; Cappel-Organon Teknika, Durham, N.C.) in blocking solution. After thorough rinsing, sections were reacted in substrate consisting of 0.5 mg diaminobenzidine (DAB)/ml of 1% $H_2O_2$ in 0.1 M Tris-HCl for 3 minutes. Immunoreactive iNOS was identified by the formation of a brown precipitate from this reaction. Samples from all five groups of patients were tested in each experiment to avoid misinterpretation of interexperimental variation in staining intensities as differences between the groups.

Immunostaining controls routinely performed on each sample involved incubation in blocking solution overnight in place of the primary antibody. The specificity of the antisera was verified by substitution of the same concentration of normal rabbit IgG as was used for the anti iNOS IgG, which produced no discernible staining. The lack of cross-reactivity of this antiserum with ecNOS was confirmed by the absence of staining of vascular endothelium in the myometrial sections and by Western blotting. The lack of cross-reactivity with ncNOS was confirmed by Western blotting since ncNOS was not detectable in the myometrial samples that were positive for iNos. Also, the specificity of the immunostaining for iNOS was verified in a few samples using a different iNOS antisera, a mouse monoclonal antibody to iNOS (No. 32020; Transduction Labs) that is affinity-purified against the immunogen, and has been previously reported in *BBRC*, 191:89 (1993) to be specific for iNOS in humans. Sections were incubated with this antibody overnight at 4° C. at 2.5 µg/ml diluted in 2% normal horse serum in TBS. Section s were then reacted with an avidin-biotin peroxidase system for mouse IgG (Vecatastain ABC Elite Kit; Vector Laboratories, Inc., Burlingame, Calif.), according to the manufacturer's instructions. Staining was completed using the same DAB formulation as above for 5 minutes.

In all samples, separate sections were stained with Gill's hematoxylin No. 2 and eosin to confirm histological structures. To aid in the identification of DAB immunoreactive cells, some sections were lightly counterstained with Gill's hematoxylin No. 2 to toluidine blue.

Although qualitative differences in iNOS staining were readily apparent, cells containing iNOS were quantified morphometrically. Immunostained sections without counterstain were examined under high power (×312) with a light microscope fitted with a Weibel reticule. For each specimen, the proportion of immunostained cells in five randomly selected fields was determined and expressed as a percentage. Significant differences between groups were assessed by analysis of variance (StatView; Abacus Concepts In., Berkeley, Calif.).

Western blotting

Myometrial protein extracts were prepared by homogenizing tissue in 5 vol (1 ml/g wet wt) of boiling 10 mM Tris HCl (pH 7.4) containing 1% SDS, heating the homogenate in a microwave oven for 10 sec, and then removing insoluble debris by centrifugation at 7,500×g for 15 min at 15° C. Protein concentration was determined using protein reagent (Bio-Rad Laboratories, Richmond, Calif.) and bovine serum albumin reference standard. Electrophoresis was performed using 100 µg aliquots of protein extract in 1×loading buffer (final concentrations: 12.5 mM Tris-HCl, pH 6.8, 0.4% SDS, 2% glycerol, 1% 2-mercaptoethanol, and 0.5% bromphenol blue) in a 6% SDS-PAGE gel.

Western blotting was performed after electrophoretic transfer of resolved proteins onto Immobilon-P paper (Millipore Corp., Bedford Mass.). An affinity-purified (against the peptide immunogen) rabbit polyclonal antibody to human iNOS (No. SC-649; Santa Cruz Biotechnology, Santa Cruz, Calif.) was used at a concentration of 2 µg/ml. Peroxidase-conjugated donkey anti-rabbit secondary antibody (Amersham Corp., Arlington Heights, Ill.) was detected (Supersignal CL-HRP Substrate System: Pierce, Rockford, Ill.). Specificity of the antisera was assessed by use of positive and negative control antigens that confirmed selectivity for human iNOS, the lack of reactivity with either murine iNOS or other NOS isoforms, and the lack of the signal from preimmune serum. Protein extracts from DLD-1 human colorectal carcinoma cells induced to express iNOS with cytokines served as the positive control for human iNOS. Quantitation of the autoradiographic signals was performed using a scanning densitometer, and the relative optical density of the iNOS band for equal areas of several specimens from each group was compared by analysis of variance. Data are expressed as means ±SE.

EXAMPLE 4

Diagnostic Methods for Detection of Nitric Oxide in Plasma and Urine

This example provides a description of diagnostic methods for detection of nitric oxide in human plasma and urine.

Spectrophotometric Method for Detection of NO in Urine

In this method, nitric oxide in urine is determined as the total amount of nitrite and nitrate. Equal amounts of urine and Griess reagent containing one part of 1% sulfanilamide in water and one part of 0.1% naphtylethylenediamine in 5% phosphoric acid are mixed. The reaction mixture is incubated at 24° C. for 10 minutes. The specific optical absorption ($OD_{540}$) of the diazo-coupling structure is determined spectrophotometrically.

Results are compared to control values of nitrite and nitrate in urine and plasma obtained from pregnant women and statistically standardized.

For statistical standardization and extrapolation to NO myometrium levels, the levels of $NO_2/NO_3$ from 50 to 100 healthy nonpregnant women, 50–100 pregnant women, 50–100 pregnant women in term labor and 50–100 pregnant women in preterm labor are tested and statistical differences between these values are determined. These levels are then correlated with the corresponding myometrical values of iNOS.

Liquid Chromatography Method for Detection of Nitrate and Nitrite in Plasma and Urine Blood and/or urine samples are collected from a pregnant patient.

Plasma is diluted with an equal volume of water, and the proteins are removed by centrifugation for 45 minutes at 7500 g through a 10K filter (Filtron Corp, Northborough, Mass.). A 20-µL sample of the ultrafiltrate is injected into a chromatography system using a 50-mm column of IC-Pak A (Waters, Milford, Mass.) as the solid phase and 1 mmol/L phosphate buffer pH 9 as the mobile phase. Quantitative analysis is performed against external or internal standards with UV absorbance at 214 nm.

Urine samples are diluted with 25 vol water before being injected into the chematography system and quantitatively analyzed as above.

Obtained results are compared to standard values of pregnant women. In this method, the detection limit for nitrate and nitrite, in plasma as well as in urine, is about 0.5 µmol/L. The values of healthy nonpregnant women are between 1.3–13 µmols/L of nitrite of plasma and 4–45 µmol/L of nitrate in plasma with cumulative value for nitrite/nitrate 23.9 µmols/L of plasma and 4 µmols/L for nitrite, 990 µmoles/liter for nitrate and cumulative value 994 µmoles/L in urine. The method is therefore sufficiently sensitive to detect urine $NO_2/NO_3/L$.

The chromatographic analyses of nitrite and nitrate in plasma and urine may be verified with gas chromatography/mass spectrometry (GC/MS) methods using purified samples of plasma or urine prepared as above. The GC/MS method is 5 times more sensitive and more suitable for detection of lower amounts of nitrate or nitrite.

For analysis of nitrate, a 150-µL portion of the sample is added with a known amount of $K^{15}NO_3$ (Sigma Chemical Co, St. Louis, Mo.) as internal standard. Endogenous and added nitrate are subsequently converted to nitrotoluene by shaking the ultrafiltrate for 20 minutes with 500 µL toluene and 200 µL concentrated $H_2SO_4$. The organic phase is then separated and 10 vol acetonitrile is added. A 1 to 2 µL of the portion is injected to gas chromatograph equipped with a 25-m SPB 5 capillary column operated isothermally at 85 µC. Gas chromatograph is connected to a mass spectrometer operated in the negative ion-chemical ionization mode using methane as a reactant gas and selective monitoring of mass/equivalent (m/e) 136 for endogenous nitrate and m/e 137 for the $^{15}$N-labeled internal standard. The detection limit of GC/MS for nitrate is 0.1 µmol/L.

For analysis of nitrite, a 200-µL portion of the sample is added with a known amount of $K^{15}NO_2$ (Sigma) as internal standard. Endogenous and added nitrite are subsequently converted to tetrazolo[1.5-∂]phthalazine by addition of equal volumes of 2N hydrochloric acid and an excess of hydralazine in 0.1N hydrochloric acid. After 15 minutes, reaction products were extracted at pH 10.5 into an equal volume of toluene. A 1 to 2-µL portion was injected into the GC/MS system described above, with selective monitoring of m/e 171 for endogenous nitrite and m/e 172 for the $^{15}$N-labeled internal standard. The detection limit for nitrite is 0.03 µmol/L.

Detection of Nitrite and Nitrate in Plasma by the Griess Reaction

The method described in *Clin. Chem*, 41:892 (1995) is modified for routine clinical testing. Plasma is obtained from the full blood by using heparin as anticoagulant.

Nitrite determination

Plasma is diluted fourfold with distilled water and deproteinized by adding 1/20th volume of zinc sulfate (300 g/L) to give a final concentration of 15 g/L. After centrifugation at 10,000 g for 5 minutes at room temperature (or 1000 g for 15 minutes), 100 µL of supernate is applied to a microtiter plate well, followed by 100 µL of Griess reagent (1 g/L sulfanilamide, 25 g/L phosphoric acid, and 0.1 g/L N-1-naphthylethylenediamine). After 10 minutes of color development at room temperature, the absorbance is measured on a microplate reader, such as, for example, Titertek Multiskan MCC/340; Flow Lab, McLean, Va., at a wavelength of 540 nm. Each sample is assayed in duplicate wells. Background values are obtained by treating samples as described but using 25 g phosphoric acid without sulfanilamide and napthylethylene diamine. Calibration curves are made with sodium nitrite and potassium nitrate in distilled water (linear range 0–100 µmol/L). The detection limit of the method is ~1.5 µmol/L in distilled water. In all these specimens, maximal absorbance occurs at 540 nm. The molar absorptivity of the colored product is approximately 39 500 L mol$^{-1}$ cm$^{-1}$.

Nitrate determination

Nitrate is measured as nitrite after enzymic conversion by nitrate reductase (EC 1.6.6.2). 100 µL of plasma is diluted fourfold with distilled water. NADPH, FAD, and nitrate reductase from Aspergillus spp. (Boehringer Mannheim, Mannheim, Germany) are added to yield final concentrations of 50 µmol/L, 5 µmol/L and 200 U/L, respectively. Samples are subsequently incubated for 20 minutes at 37° C., and then mixed with lactate dehydrogenase from rabbit muscle (Boehringer Mannheim) at a final concentration of 10 mg/L and sodium pyruvate at a final concentration of 10 mmol/L. Samples are further incubated for 5 minutes at 37° C. to oxidize NADPH, deproteinized, and assayed with Griess reagent as described above. Values obtained by this procedure represent the sum of nitrite and nitrate. Nitrate concentrations are obtained by subtracting nitrite concentrations from the total nitrate+nitrite concentrations. A decrease of nitrite/nitrate cumulative value is interpreted as indication of preterm labor initiation or risk.

Enzymatic Determination of Nitrate in Serum and Urine

The method is according to Clin. Chem., 41:904 (1995), modified for clinical use.

One to two milliliters of blood is drawn and serum is separated. Serum (0.1 ml) is added to laboratory tubes containing 250 µL of 100 mmol/L potassium phosphate buffer (pH 7.5), 50 µL of distilled water, 50 µL of 0.2 mmol/L FAD, and 10 µL of 12 mmol/L β-NADPH. 40 µL of 500 U/L nitrate reductase is added, mixed and placed in the dark. After 45 minutes the mixture is subjected to the UV spectrophotometric detection of the absorbance at 340 nm.

For each sample, a sample control of a corresponding serum is treated in the same way except that nitrate reductase is omitted and replaced by distilled water to the same final reaction volume.

Additionally, for accuracy, the reagent control is prepared. To 250 µL of potassium phosphate buffer, 50 µL of 0.2 mmol/L FAD, and 10 µL of 12 mmol/L β-NADPH, 150 µL of distilled water is added in the presence or absence of 40 µL of 500 U/L nitrate reductase.

The absorbance at 340 nm of each sample is determined. The value is subtracted from the A$_{340}$ of the corresponding sample control and the absorbance change of the reagent control is subtracted. Obtained values are compared and read from the standard curves.

EXAMPLE 5

Determination of Citrulline or Arginine in Plasma

This example describes method for detection of NO coproduct citrulline substrate and arginine in human plasma.

Determination of Citrulline in Plasma

Blood is drawn and plasma isolated. Plasma (0.1 ml) is mixed with 200 µL of 10% (w/v) TCA. The mixture is let stand for 10 minutes, then the solution is centrifuged at 10000 g for 3 minutes. Supernatant is removed and analyzed by HPLC with a cation-exchange resin column. Citrulline is eluted with citrate buffer solution.

The method detects citrulline in the range from 2.5 to 500 µM.

Determination of Arginine in Plasma

Plasma (0.1 ml) is adjusted to pH 2.5 with 0.1 M HCl and applied to a Dowex cation exchange resin column AG 50W-X8, previously washed with Milli-Q+water. The column is washed with water and eluted with 2 ml 2M ammonium hydroxide into 3 ml Reacti-vials. The samples are freeze-dried and the residue heated at 100° C. for 30 minutes with 200 µl of TFAA used for derivatization of arginine. The solution is then vacuum dried with oxygen-free nitrogen (OFN), redissolved in acetonitrile and 2 µl amount is injected onto the GC-MS.

EXAMPLE 6

Chemiluminescence Method for Detection of Nitric Oxide

Method for detection of nitric oxide using chemiluminescence is essentially that described in Analytical Biochem., 212: 359 (1993).

Nitrate and nitrite are converted into nitric oxide using Aspergillus nitrate reductase. A nitrogen oxide analyzer is used to determine the concentration of nitric oxide by chemiluminescence after reaction with ozone.

Chemiluminescence apparatus for detection of nitric oxide is described fully in FASEB, 7: 349 (1993) and is hereby incorporated by reference.

Detection threshold of the method is within $10^{-13}$M of nitric oxide.

EXAMPLE 7

Electron Paramagnetic Resonance Method for Detection of Nitric Oxide

This example illustrates electron paramagnetic resonance method for in vivo and ex vivo detection of nitric oxide in human patients. The method described in Biochem. Biophys. Acta, 1272:29 (1995) is modified for human use.

Human patient has venous catheter introduced and a solution containing $^{15}$N arginine (5–100 mg) in saline, and of 0.4 ml of the [(MGD)$_2$/FE] complex (326 mg/kg of MGD and 34 mg/kg of FeSO$_4$) is injected. Immediately after injection, the patient is transferred to the S-band EPR spectrometer and the arm with catheter is immobilized by taping down with a thin and narrow plexiglass plate and then placed inside the resonator. The in vivo EPR signal is recorded at 1 or 2 hours after the injection of the [(MGD)$_2$/Fe] complex. The concentrations of the [(MGD)$_2$/Fe—NO] complex in the urine samples are calculated by comparing the signal intensities obtained from the samples to the signal intensity of a standard solution containing 0.1 mM of the [(MGD)$_2$/Fe—NO] complex.

For in vivo measurement of [(MGD)$_2$/Fe—NO] levels in the human circulation, the noninvasive in vivo EPR spectra are recorded with an EPR spectrometer equipped with an S-band microwave bridge and a low-frequency loop-gap resonator with a 4-mm loop with a length of 1 cm, operating at 3.5 GHz. Instrument settings include 100-G field scan, 30-s scan time, 0.1-s time constant, 2.5-G modulation amplitude, 100-KHz modulation frequency and 25-mW microwave power. The measured unloaded Q of the empty resonator was 3000 and the loaded Q was 400.

For ex vivo measurement, urine analyses are collected. The urine sample which is usually dark brown due to the presence of [(MGD)$_2$/Fe] complex is transferred to a quartz flat cell for EPR measurement. The spectra are recorded at 22° C. with an X-band EPR spectrometer, operating at 9.5 GHZ. Instrument settings include 100-G field scan, 4-min scan time, 0.5-s time constant, 2.5-G modulation amplitude, 100 KHz modulation frequency and 100-mW microwave power.

What is claimed is:

1. A non-invasive non-surgical method for detection, diagnosis or prediction of term or pre-term labor in a pregnant female, said method comprising steps:
   (a) obtaining a sample of blood, plasma, serum, urine or saliva from the pregnant female;
   (b) subjecting said sample to a procedure detecting a level of nitric oxide, arginine or citrulline, or activity of nitric oxide synthase, expression of nitric oxide synthase or conversion of nitric oxide to its metabolites nitrate and nitrite in said blood, plasma, serum, urine, saliva or a tissue sample obtained from the pregnant female;
   (c) detecting, diagnosing or predicting said term or pre-term labor by comparing levels of nitric oxide, arginine or citrulline, or activity of nitric oxide synthase, expression of nitric oxide synthase or conversion of nitric oxide to its metabolites nitrate and nitrite obtained from a tested female to levels obtained from a pregnant non-laboring female.

2. The method of claim 1 wherein the term or pre-term labor is detected, diagnosed or predicted by determination of decreased levels of nitric oxide, decreased conversion of arginine to citrulline, decreased conversion of nitric oxide to nitrate and nitrite markers and by detection of lower levels of nitrate and nitrite markers in plasma, serum or urine when compared to such levels obtained from the pregnant non-laboring female.

3. The method of claims 2
   wherein the conversion of nitric oxide to nitrate and nitrite in urine is detected spectrophotometrically using the Griess reagent;
   wherein the conversion of nitric oxide to nitrate and nitrite in plasma or urine is detected by liquid chromatography or by the Griess reaction;
   wherein nitrate in serum or urine is detected enzymatically by using nitrate reductase; and
   wherein obtained results in each detection method are compared to standard values of nitrate and nitrite in pregnant non-laboring females.

4. The method of claim 3 wherein decrease of a cumulative nitrate and nitrite value compared to standard values in the pregnant female indicates the presence, onset or risk of term or pre-term labor.

5. The method of claim 1 wherein the term or pre-term labor is detected, diagnosed or predicted by determination of arginine or citrulline in plasma, serum or urine.

6. The method of claim 5 wherein the citrulline is detected by high pressure liquid chromatography using a cation-exchange resin column and wherein arginine is detected by derivatization and gas chromatography-mass spectrometry or wherein the level of nitric oxide is detected by conversion assay of labeled arginine to labeled citrulline and nitric oxide.

7. The method of claim 1 wherein the term or pre-term labor is detected, diagnosed or predicted by determination of nitric oxide synthase activity.

8. The method of claim 7 wherein the activity of nitric oxide synthase is determined morphologically by staining with nitro blue tetrazolium dye, by measurement of conversion of labeled arginine to labeled citrulline, by Western blot analysis, by immunolocalization of inducible nitric oxide synthase (iNOS), by expression of myometrium nitric oxide synthase or by immunohistochemistry.

9. The method of claim 8 wherein a decreased nitric oxide synthase activity or a decreased expression in nitric oxide compared to standard values in the pregnant female indicates the presence, onset or risk of term or pre-term labor.

10. The method of claim 9 wherein the nitric oxide synthase activity is detected by conversion of $^3$H-labeled arginine to $^3$H labeled citrulline.

11. The method of claim 1 wherein the term or pre-term labor is detected, diagnosed or predicted by determination of a nitric oxide level.

12. The method of claim 11 wherein the nitric oxide level is detected by chemiluminescence or by electron paramagnetic resonance method.

13. The method of claim 12 wherein nitric oxide is detected by chemiluminescence after reaction of nitric oxide with ozone.

14. the method of claim 12 wherein nitric oxide is detected by electron paramagnetic resonance method in vivo in blood circulation or ex vivo in urine.

15. A method for detection, diagnosis and prediction of pre-term or term labor onset, said method comprising steps:
   (a) monitoring a level of nitric oxide or production of inducible nitric oxide synthase (iNos);
   (b) comparing the obtained level of nitric oxide or inducible nitric oxide synthase to a standard level of pregnant non-laboring females.

* * * * *